US011993816B2

(12) United States Patent
Taylor et al.

(10) Patent No.: US 11,993,816 B2
(45) Date of Patent: *May 28, 2024

(54) CIRCULATING MICRORNA AS BIOMARKERS FOR ENDOMETRIOSIS

(71) Applicant: Yale University, New Haven, CT (US)

(72) Inventors: Hugh Taylor, Easton, CT (US); SiHyun Cho, Orange, CT (US)

(73) Assignee: Yale University

( * ) Notice: Subject to any disclaimer, the term of this patent is extended or adjusted under 35 U.S.C. 154(b) by 0 days.

This patent is subject to a terminal disclaimer.

(21) Appl. No.: 15/129,663

(22) PCT Filed: Mar. 27, 2015

(86) PCT No.: PCT/US2015/022986
§ 371 (c)(1),
(2) Date: Sep. 27, 2016

(87) PCT Pub. No.: WO2015/148919
PCT Pub. Date: Oct. 1, 2015

(65) Prior Publication Data
US 2017/0175190 A1 Jun. 22, 2017

Related U.S. Application Data

(60) Provisional application No. 61/971,092, filed on Mar. 27, 2014.

(51) Int. Cl.
*C12Q 1/68* (2018.01)
*C12Q 1/6883* (2018.01)
*G01N 33/574* (2006.01)

(52) U.S. Cl.
CPC ...... *C12Q 1/6883* (2013.01); *C12Q 2600/118* (2013.01); *C12Q 2600/156* (2013.01); *C12Q 2600/158* (2013.01); *C12Q 2600/178* (2013.01)

(58) Field of Classification Search
CPC ........ C12Q 2600/158; C12Q 2600/178; C12Q 2600/156; C12Q 1/6883
See application file for complete search history.

(56) References Cited

U.S. PATENT DOCUMENTS

| | | |
|---|---|---|
| 10,982,282 B2 | 4/2021 | Taylor |
| 11,220,713 B2 | 1/2022 | Taylor |
| 11,315,660 B2 | 4/2022 | Taylor |
| 2009/0317820 A1 | 12/2009 | Wong |
| 2012/0093936 A1 | 4/2012 | Lindenberg |

(Continued)

FOREIGN PATENT DOCUMENTS

| | | |
|---|---|---|
| CN | 103237901 A | 8/2013 |
| EP | 2924126 | 9/2015 |

(Continued)

OTHER PUBLICATIONS

Afshar et al. (Papio anubis. Biol Reprod. Feb. 2013;88(2):44).*

(Continued)

*Primary Examiner* — Terra C Gibbs
(74) *Attorney, Agent, or Firm* — Riverside Law LLP

(57) ABSTRACT

The invention includes compositions and methods useful for the diagnosis, assessment, and characterization of endometriosis in a subject in need thereof, based upon the expression level of at least one miRNA that is associated with endometriosis.

51 Claims, 4 Drawing Sheets

Specification includes a Sequence Listing.

(56) References Cited

U.S. PATENT DOCUMENTS

| | | |
|---|---|---|
| 2014/0024590 A1 | 1/2014 | Weidhaas |
| 2014/0342937 A1 | 11/2014 | Jeanson-Leh |
| 2015/0267257 A1 | 9/2015 | Nagarkatti et al. |
| 2016/0251718 A1 | 9/2016 | Giudice et al. |
| 2017/0175190 A1 | 6/2017 | Taylor |
| 2018/0127828 A1 | 5/2018 | Belli |
| 2019/0276893 A1 | 9/2019 | Taylor |
| 2020/0206303 A1 | 7/2020 | Bowerman |
| 2020/0321077 A1 | 10/2020 | Taylor et al. |
| 2021/0180134 A1 | 6/2021 | Taylor |
| 2022/0049312 A1 | 2/2022 | Taylor |

FOREIGN PATENT DOCUMENTS

| | | |
|---|---|---|
| EP | 2924126 B1 | 4/2018 |
| JP | 2014513521 A | 6/2014 |
| JP | 2015504655 A | 2/2015 |
| WO | WO-2010056337 A2 | 5/2010 |
| WO | 2012103355 A2 | 8/2012 |
| WO | 2012112883 | 8/2012 |
| WO | 2013148151 A1 | 10/2013 |
| WO | 2015073972 A1 | 5/2015 |
| WO | WO-2015128671 A1 | 9/2015 |
| WO | WO-2015148919 A2 | 10/2015 |
| WO | 2018044979 | 3/2018 |
| WO | 2019046494 | 3/2019 |
| WO | 2020092672 | 5/2020 |
| WO | WO-2020223238 A1 | 11/2020 |

OTHER PUBLICATIONS

Laudanski et al. (Hum Reprod. Aug. 2009;24(8): 1880-90).*
Cheng et al. (J Pathol 2011; 224:261-269).*
MedicalNewsToday downloaded from Sputum: Definition, colors, causes, and when to see a doctor (medicalnewstoday.com) on Dec. 1, 2021.*
Voelkerding et al. (Clinical Chemistry, 2009 vol. 55:641-658).*
Azmy et al. (Medical Research Journal: Dec. 2012—vol. 11:pp. 1-13).*
Kennedy et al. (Hum Reprod., 2005 vol. 20:2698-2704).*
Chang et al. BMPR1B Up-Regulation via a miRNA Binding Site Variation Defines Endometriosis Susceptibility and CA125 Levels. PLoS ONE 2013, 8:e80630-e80630.
Chen et al. MiR-125b regulates endometrial receptivity by targeting MMP26 in women undergoing IVF-ET with elevated progesterone on HCG priming day. Scientific reports 6 (2016): 25302.
Cho et al. Aromatase inhibitor regulates let-7 expression and let-7f-induced cell migration in endometrial cells from women with endometriosis. Fertility and sterility 106.3 (2016): 673-680.
EP15769372.2 Extended Search Report dated Sep. 8, 2017.
Ghazal et al. H19 lncRNA alters stromal cell growth via IGF signaling in the endometrium of women with endometriosis. EMBO molecular medicine 7.8 (2015): 996-1003.
Graham et al. The expression of microRNA-451 in human endometriotic lesions is inversely related to that of macrophage migration inhibitory factor (MIF) and regulates MIF expression and modulation of epithelial cell survival. Human Reproduction 30.3 (2015): 642-652.
Joshi et al. Altered expression of microRNA-451 in eutopic endometrium of baboons (*Papio anubis*) with endometriosis. Human Reproduction 30.12 (2015): 2881-2891.
Nematian et al. Systemic inflammation induced by microRNAs: endometriosis-derived alterations in circulating microRNA 125b-5p and Let-7b-5p regulate macrophage cytokine production. The Journal of Clinical Endocrinology & Metabolism 103.1 (2017): 64-74.
Wen-Tao Wang et al, "Circulating MicroRNAs Identified in a Genome-Wide Serum MicroRNA Expression Analysis as Noninvasive Biomarkers for Endometriosis", Journal of Clinical Endocrinology & Metabolism, (20130101), vol. 98, No. 1, doi: 10.1210/jc.2012-2415, ISSN 0021-972X, pp. 281-289, XP055127854.
Rafaella Petracco et al, "MicroRNA 135 Regulates HOXA10 Expression in Endometriosis", Journal of Clinical Endocrinology & Metabolism, (20111201), vol. 96, No. 12, doi:10.1210/jc.2011-1231, ISSN 0021-972X, pp. E1925-E1933, XP055187310.
Olga Grechukhina et al, "A polymorphism in a let-7 microRNA binding site of KRAS in women with endometriosis", EMBO Molecular Medicine, (20120203), vol. 4, No. 3, doi:10.1002/emmm. 201100200, ISSN 1757-4676, pp. 206-217, XP055026349.
Ruan Yu et al, "[Study on microRNA expression in endometrium of luteal phase and its relationship with infertility of endometriosis]", Chung-Hua Fu Ch'an K'o Tsa Chih—Chinese Journal of Obstetricsand Gyneco, Chinese Medical Journals Publ. House, CN, (20131201), vol. 48, No. 12, ISSN 0529-567X, pp. 907-910, XP008170439.
Aitana Braza-Bols et al, "MicroRNA expression profile in endometriosis: its relation to angiogenesis and fibrinolytic factors", Human Reproduction, GB, (20140306), vol. 29, No. 5, doi:10.1093/humrep/deu019, ISSN 0268-1161, pp. 978-988, XP055402965.
Cho Sihyun et al, "Circulating microRNAs as potential biomarkers for endometriosis", Fertility and Sterility, (20150313), vol. 103, No. 5, doi:10.1016/J.FERTNSTERT.2015.02.013, ISSN 0015-0282, p. 1252, XP029155696.
Vodolazkaia et al., "Evaluation of a panel of 28 biomarkers for the non-invasive diagnosis of endometriosis." Hum Reprod, 27: 2698-2711, Jun. 26, 2012.
Iorio et al., "MicroRNA gene expression deregulation in human breast cancer." Cancer Res, 65: 7065-7070, Aug. 15, 2005.
Akao et al., 2007, "MicroRNA-143 and -145 in colon cancer." DNA Cell Biol, 26: 311-320.
Yang et al., "MicroRNA expression profiling in human ovarian cancer: miR-214 induces cell survival and cisplatin resistance by targeting PTEN." Cancer Res, 68: 425-433, Jan. 15, 2008.
Small et al., "Pervasive roles of microRNAs in cardiovascular biology." Nature, 469: 336-342, Jan. 20, 2011.
Brest et al., "A synonymous variant in IRGM alters a binding site for miR-196 and causes deregulation of IRGM-dependentxenophagy in Crohn's disease." Nat Genet, 43: 242-245, Jan. 10, 2011.
Yang et al., "MicroRNA microarray identifies Let-7i as a novel biomarker and therapeutic target in human epithelial ovarian cancer." Cancer Res, 68: 10307-10314.
Marsh et al., "Differential expression of microRNA species in human uterine leiomyoma versus normal myometrium.." Fertil Steril, 89: 1771-1776, Dec. 15, 2008.
Mitchell et al., "Circulating microRNAs as stable blood-based markers for cancer detection." Proc Natl Acad Sci USA, 105: 10513-10518, May 12, 2008.
Lawrie et al., "Detection of elevated levels of tumour-associated microRNAs in serum of patients with diffuse large B-cell lymphoma.." Br J Haematol, 141: 672-675, Jan. 2, 2008.
Nakasa et al., "Expression of microRNA-146 in rheumatoid arthritis synovial tissue." Arthritis Rheum, 58: 1284-1292, May 2008.
Wang et al., "Serum miR-146a and miR-223 as potential new biomarkers for sepsis." Biochem Biophys Res Commun, 394: 184-188, Feb. 2010.
D'Alessandra et al., 2010, "Circulating microRNAs are new and sensitive biomarkers of myocardial infarction." Eur Heart J, 31: 2765-2773.
Resnick et al., 2008, "The detection of differentially expressed microRNAs from the serum of ovarian cancer patients using a novel real-time PCR platform." Gynecol Oncol, 112: 55-59.
Wang et al., "Correlation and quantitation of microRNA aberrant expression in tissues and sera from patients with breast tumor." Gynecol Oncol, 119: 586-593, Jul. 2010.
Teague et al., "MicroRNA-regulated pathways associated with endometriosis." Mol Endocrinol, 23: 265-275, Dec. 2008.
Pan et al., "The expression profile of micro-RNA in endometrium and endometriosis and the influence of ovarian steroids on their expression." Mol Hum Reprod, 13: 797-806 (Retracted), Aug. 31, 2007.
Ramon et al., "microRNAs expression in endometriosis and their relation to angiogenic factors." Hum Reprod, 26: 1082-1090, Jan. 17, 2011.

(56) References Cited

OTHER PUBLICATIONS

Dai et al., 2012, MiR-199a attenuates endometrial stromal cell invasiveness through suppression of the IKKβ/NF-κB pathway and reduced interleukin-8 expression. Mol Hum Reprod, 18: 136-145.
Teague et al., 2010, The role of microRNAs in endometriosis and associated reproductive conditions. Hum Reprod Update, 16: 142-165.
Mol et al., "The performance of CA-125 measurement in the detection of endometriosis: a meta-analysis." Fertil Steril, 70: 1101-1108, Dec. 1998.
Tang et al., "MiR-135a functions as a tumor suppressor in epithelial ovarian cancer and regulates HOXA10 expression." Cell Signal, 26: 1420-1426, Mar. 2014.
Jarry et al., 2014, The validity of circulating microRNAs in oncology: five years of challenges and contradictions. Mol Oncol, 8: 819-829.
Nagel et al., "Regulation of the adenomatous polyposis coli gene by the miR-135 family in colorectal cancer." Cancer Res, 68: 5795-5802, Jul. 15, 2008.
Zhu et al., 2008, "Heme oxygenase-1 suppresses hepatitis C virus replication and increases resistance of hepatocytes to oxidant injury." Hepatology, 48: 1430-1439.
Hou et al., "The let-7 microRNA enhances heme oxygenase-1 by suppressing Bach1 and attenuates oxidant injury in human hepatocytes." Biochim Biophys Acta, 1819: 1113-1122, Jun. 2012.
Bell et al., 2013, "Insulin-like growth factor 2 mRNA-binding proteins (IGF2BPs): post-transcriptional drivers of cancer progression?" Cell Mol Life Sci, 70: 2657-2675.
Mongroo et al., "IMP-1 displays cross-talk with K-Ras and modulates colon cancer cell survival through the novel proapoptotic protein CYFIP2." Cancer Res, 71: 2172-2182, Jan. 20, 2011.
Suryawanshi et al., "Plasma microRNAs as novel biomarkers for endometriosis and endometriosis-associated ovarian cancer." Clin Cancer Res, 19: 1213-1224, Jan. 29, 2013.
May et al., "Peripheral biomarkers of endometriosis: a systematic review." Hum Reprod Update, 16: 651-674, May 12, 2010.
Rekker et al., 2013, "Circulating microRNA Profile throughout the menstrual cycle." PLoS One, 8: e81166, (6 pages).
Weber et al., "The MicroRNA Spectrum in 12 Body Fluids", Clinical Chemistry 56:11; pp. 1733-1741 (2010).
D'Hooghe, et al. Lack of an Association between a Polymorphism in the KRAS 3' Untranslated Region (rs61764370) and Endometriosis in a Large European Case-Control Study.Gynecologic and obstetric investigation 84.6 (2019): 575-582.
Luong, et al. No evidence for genetic association with the let-7 microRNA-binding site or other common KRAS variants in risk of endometriosis.Human reproduction 27.12 (2012): 3616-3621.
Co-pending U.S. Appl. No. 16/860,792, filed Apr. 28, 2020 (82 pages).
PCT/US2015/022986 International search report with written opinion dated Aug. 10, 2015. (11 pages).
Arroyo et al. Argonaute2 complexes carry a population of circulating microRNAs independent of vesicles in human plasma. Proc Natl Acad Sci U S A, 108:5003-5008 (2011).
Co-pending U.S. Appl. No. 17/289,882, inventor Taylor; Hugh, filed Apr. 29, 2021.
Cosar, et al. Serum microRNAs as diagnostic markers of endometriosis: a comprehensive array-based analysis. Fertil Steril. Aug. 2016; 106(2):402-9.
EP20194688.6 Extended European Search Report dated Feb. 22, 2021.
Gallo et al. The majority of microRNAs detectable in serum and saliva is concentrated in exosomes. PLoS One, 7: e30679 (2012).
Jia et al. Plasma miR-17-5p, miR-20a and miR-22 are down-regulated in women with endometriosis. Hum Reprod, 28:322-330 (2013).
U.S. Appl. No. 16/329,436 Notice of Allowance dated Feb. 1, 2021.
U.S. Appl. No. 16/329,436 Notice of Allowance dated Jan. 27, 2021.
U.S. Appl. No. 17/184,894 Notice of Allowance dated Sep. 21, 2021.

Co-pending U.S. Appl. No. 17/703,321, inventors Taylor; Hugh et al., filed Mar. 24, 2022.
Co-pending U.S. Appl. No. 17/834,762, inventors Bowerman; Heather et al., filed Jun. 7, 2022.
Office Action (Non-Final Rejection) dated Dec. 19, 2023 for U.S. Appl. No. 17/517,014 (pp. 1-9).
Bandiera et al., 2015, "miR-122—a key factor and therapeutic target in liver disease.." J Hepatol, 62:448-457.
Chen et al., 2008, "Characterization of microRNAs in serum: a novel class of biomarkers for diagnosis of cancer and other diseases." Cell Res, 18:997-1006.
Chen et al., 2014, "MicroRNA 125b suppresses the proliferation and osteogenic differentiation of human bone marrow derived mesenchymal stem cells." Mol Med Rep, 9(5):1820-1826.
Cho et al., 2012, "Urinary vitamin D-binding protein is elevated in patients with endometriosis." Hum Reprod, 27:515-522.
Coskun et al., 2012, "MicroRNAs in inflammatory bowel disease—pathogenesis, diagnostics and therapeutics.." World J Gastroenterol, 18:4629-4634.
Dorval et al., 2013, "Circulating microRNAs in Alzheimer's disease: the search for novel biomarkers.." Front Mol Neurosci, 6:24 (6 pages).
EP17847431.8 Extended European Search Report dated Jul. 22, 2020 (15 pages).
EP17847431.8 The Partial Supplemental European Search Report dated Apr. 8, 2020. (14 pages).
EP18852025.8 Extended Search Report dated Aug. 3, 2021.
Giray et al., 2014, "Profiles of serum microRNAs; miR-125b-5p and miR223-3p serve as novel biomarkers for HBV-positive hepatocellular carcinoma." Mol Biol Rep, 41(7):4513-4519.
Jin et al., 2013, "Circulating microRNAs: a novel class of potential biomarkers for diagnosing and prognosing central nervous system diseases.." Cell Mol Neurobiol, 5:601-613.
Lai et al., 2014, "Modulated expression of human peripheral blood microRNAs from infancy to adulthood and its role in aging." Aging Cell, 13:679-689.
Liu et al., 2014, "MicroRNAs as potential biomarkers for gastric cancer." World J Gastroenterol, 20:12007-12017.
Liu et al., 2016, "MicroRNA 451 inhibits neuroblastoma proliferation, invasion and migration by targeting macrophage migration inhibitory factor." Mol Med Rep, 13(3): 2253-60; doi: 10.3892/mmr. 4770.
Matamala et al., 2015, "Tumor microRNA expression profiling identifies circulating microRNAs for early breast cancer detection." Clin Chem, 61(8): 1098-1106.
Moustafa, et al. Accurate diagnosis of endometriosis using serum microRNAs. Am J Obstet Gynecol. Mar. 9, 2020. pii: S0002-9378(20)30321-5. doi: 10.1016/j.ajog.2020.02.050. [Epub ahead of print], 28 pages.
Mu, et al. Expression, regulation and function of MicroRNAs in endometriosis. Die Pharmazie-An International Journal of Pharmaceutical Sciences 71.8 (2016): 434-438.
Murri et al., 2013, "Effects of polycystic ovary syndrome (PCOS), sex hormones, and obesity on circulating miRNA-21, miRNA-27b, miRNA-103, and miRNA-155 expression." J Clin Endocrinol Metab, 98:E1835-1844.
Naqvi et al., 2016, "Endometriosis Located Proximal to or Remote From the Uterus Differentially Affects Uterine Gene Expression." Reprod Sci, 23:186-191.
Nisenblat, et al. Blood biomarkers for the non-invasive diagnosis of endometriosis. Cochrane Database Syst Rev. May 1, 2016;(5):CD012179. (654 pages).
Notice of Allowability dated Dec. 14, 2021 for U.S. Appl. No. 17/184,894 (pp. 1-2).
Office Action (Non-Final Rejection) dated May 24, 2023 for U.S. Appl. No. 17/517,014 (pp. 1-7).
Office Action dated Apr. 8, 2020 for U.S. Appl. No. 16/329,436 (pp. 1-19).
Office Action dated Aug. 4, 2021 for U.S. Appl. No. 17/184,894 (pp. 1-6).
Office Action dated Jul. 29, 2019 for U.S. Appl. No. 15/129,663 (pp. 1-11).

(56) References Cited

OTHER PUBLICATIONS

Office Action dated Oct. 27, 2020 for U.S. Appl. No. 16/329,436 (pp. 1-20).
PCT/US2015/022986 International Preliminary Report on Patentability dated Sep. 27, 2016. (10 pages).
PCT/US2017/049284 International Search Report and Written Opinion dated Nov. 28, 2017. (15 pages).
PCT/US2018/048649 International Search Report dated Jan. 2, 2019. (14 pages).
Reis et al., 2012, "Diagnostic value of serum activin A and follistatin levels in women with peritoneal, ovarian and deep infiltrating endometriosis." Hum Reprod, 27:1445-1450.
Sayed et al., 2014, "Diagnosis, Prognosis and Therapeutic Role of Circulating miRNAs in Cardiovascular Diseases." Heart Lung Cir, 23:503-510.
Schwarzenbach et al., 2014, "Clinical relevance of circulating cell-free microRNAs in cancer." Nat Rev Clin Oncol, 11:145-156.
Sredni et al., 2011, "A Parallel Study of mRNA and microRNA Profiling of Peripheral Blood in Young Adult Women." Front Genet, 2:49 (6 pages).
Taylor, et al. Treatment of Endometriosis-Associated Pain with Elagolix, an Oral GnRH Antagonist.. N Engl J Med. Jul. 6, 2017;377(1):28-40.
Turchinovich et al., 2011, "Characterization of extracellular circulating microRNA." Nucleic Acids Res, 39:7223-7233.
U.S. Appl. No. 15/129,663 Examiner Interview Summary dated Nov. 20, 2020, 5 pages.
Ulivi et al., 2014, "miRNAs as non-invasive biomarkers for lung cancer diagnosis." Molecules, 19:8220-8237.
Wang et al., 2012, "Circulating MIR-125b as a marker predicting chemoresistance in breast cancer." PLoS One, 7: e34210 (8 pages).
Wang et al., 2012, "Evidence for serum miR-15a and miR-16 levels as biomarkers that distinguish sepsis from systemic inflammatory response syndrome in human subjects." Clin Chem Lab Med, 50:1423-1428.
Wang et al., 2013, "Circulating microRNAs identified in a genome-wide serum microRNA expression analysis as noninvasive biomarkers for endometriosis." J Clin Endocrinol Metab, 98:281-289.
Wang et al., 2015, "MicroRNA-125b may function as an oncogene in lung cancer cells." Mol Med Rep, 11 (5):3880-3887.
Wang, et al. Analysis of Serum microRNA Profile by Solexa Sequencing in Women With Endometriosis. Reprod Sci. Oct. 2016;23(10):1359-70. doi: 10.1177/1933719116641761. Epub Jul. 13, 2016.
Xu et al., 2014, "Tumor-suppressing effects of miR451 in human osteosarcoma." Cell Biochem Biophys, 69(1):163-168.
Zhao et al., 2006, "KRAS variation and risk of endometriosis." Molecular Human Reproduction. vol. 12, No. 11, pp. 671-676.
Zhao et al., 2012, "Circulating microRNA miR-323-3p as a biomarker of ectopic pregnancy." Clin Chem, 58:896-905.
Zhu et al., 2014, Different miRNA expression profiles between human breast cancer tumors and serum.' Front Genet, 5:149, 7 pages.

* cited by examiner

```
                          SEQUENCE LISTING

<160> NUMBER OF SEQ ID NOS: 18

<210> SEQ ID NO 1
<211> LENGTH: 22
<212> TYPE: RNA
<213> ORGANISM: Artificial
<220> FEATURE:
<223> OTHER INFORMATION: Chemically synthesized

<400> SEQUENCE: 1
uugauauguu ggaugaugga gu                                              22

<210> SEQ ID NO 2
<211> LENGTH: 22
<212> TYPE: RNA
<213> ORGANISM: Artificial
<220> FEATURE:
<223> OTHER INFORMATION: Chemically synthesized

<400> SEQUENCE: 2
uugguguguu ggaugaugga gu                                              22

<210> SEQ ID NO 3
<211> LENGTH: 22
<212> TYPE: RNA
<213> ORGANISM: Artificial
<220> FEATURE:
<223> OTHER INFORMATION: Chemically synthesized

<400> SEQUENCE: 3
uugguauguu ggaugaugga gu                                              22

<210> SEQ ID NO 4
<211> LENGTH: 21
<212> TYPE: RNA
<213> ORGANISM: Artificial
<220> FEATURE:
<223> OTHER INFORMATION: Chemically synthesized

<400> SEQUENCE: 4
ugauacguug gaugauggag a                                               21

<210> SEQ ID NO 5
<211> LENGTH: 20
<212> TYPE: RNA
<213> ORGANISM: Artificial
<220> FEATURE:
<223> OTHER INFORMATION: Chemically synthesized

<400> SEQUENCE: 5
uauauguugg aggauggagu                                                 20

<210> SEQ ID NO 6
```

```
<211> LENGTH: 22
<212> TYPE: RNA
<213> ORGANISM: Artificial
<220> FEATURE:
<223> OTHER INFORMATION: Chemically synthesized

<400> SEQUENCE: 6
uugauauguu agaugaugga gu                                              22

<210> SEQ ID NO 7
<211> LENGTH: 20
<212> TYPE: RNA
<213> ORGANISM: Artificial
<220> FEATURE:
<223> OTHER INFORMATION: Chemically synthesized

<400> SEQUENCE: 7
gacauguuug augauggagu                                                 20

<210> SEQ ID NO 8
<211> LENGTH: 21
<212> TYPE: RNA
<213> ORGANISM: Artificial
<220> FEATURE:
<223> OTHER INFORMATION: Chemically synthesized

<400> SEQUENCE: 8
ugucguguuu guugauggag u                                               21

<210> SEQ ID NO 9
<211> LENGTH: 22
<212> TYPE: DNA
<213> ORGANISM: Artificial
<220> FEATURE:
<223> OTHER INFORMATION: Chemically synthesized

<400> SEQUENCE: 9
tgaggtagta ggttgtatag tt                                              22

<210> SEQ ID NO 10
<211> LENGTH: 22
<212> TYPE: DNA
<213> ORGANISM: Artificial
<220> FEATURE:
<223> OTHER INFORMATION: Chemically synthesized

<400> SEQUENCE: 10
tgaggtagta ggttgtgtgg tt                                              22

<210> SEQ ID NO 11
<211> LENGTH: 22
<212> TYPE: DNA
<213> ORGANISM: Artificial
<220> FEATURE:
<223> OTHER INFORMATION: Chemically synthesized

<400> SEQUENCE: 11
tgaggtagta ggttgtatgg tt                                              22

<210> SEQ ID NO 12
<211> LENGTH: 22
<212> TYPE: DNA
<213> ORGANISM: Artificial
<220> FEATURE:
<223> OTHER INFORMATION: Chemically synthesized

<400> SEQUENCE: 12
```
agaggtagta ggttgcatag tt                                              22

<210> SEQ ID NO 13
<211> LENGTH: 22
<212> TYPE: DNA
<213> ORGANISM: Artificial
<220> FEATURE:
<223> OTHER INFORMATION: Chemically synthesized

<400> SEQUENCE: 13
tgaggtagga ggttgtatag tt                                              22

<210> SEQ ID NO 14
<211> LENGTH: 22
<212> TYPE: DNA
<213> ORGANISM: Artificial
<220> FEATURE:
<223> OTHER INFORMATION: Chemically synthesized

<400> SEQUENCE: 14
tgaggtagta gattgtatag tt                                              22

<210> SEQ ID NO 15
<211> LENGTH: 23
<212> TYPE: DNA
<213> ORGANISM: Artificial
<220> FEATURE:
<223> OTHER INFORMATION: Chemically synthesized

<400> SEQUENCE: 15
tatggctttt tattcctatg tga                                             23

<210> SEQ ID NO 16
<211> LENGTH: 23
<212> TYPE: DNA
<213> ORGANISM: Artificial
<220> FEATURE:
<223> OTHER INFORMATION: Chemically synthesized

<400> SEQUENCE: 16
tatggctttt cattcctatg tga                                             23

<210> SEQ ID NO 17
<211> LENGTH: 17
<212> TYPE: DNA
<213> ORGANISM: Artificial
<220> FEATURE:
<223> OTHER INFORMATION: Chemically synthesized

<400> SEQUENCE: 17
ctcgcttcgg cagcaca                                                    17

<210> SEQ ID NO 18
<211> LENGTH: 20
<212> TYPE: DNA
<213> ORGANISM: Artificial
<220> FEATURE:
<223> OTHER INFORMATION: Chemically synthesized

<400> SEQUENCE: 18
aacgcttcac gaatttgcgt                                                 20

CIRCULATING MICRORNA AS BIOMARKERS FOR ENDOMETRIOSIS

CROSS-REFERENCE TO RELATED APPLICATIONS

This application is the U.S. national phase application filed under 35 U.S.C. § 371 claiming benefit to International Patent Application No. PCT/US15/22986, filed Mar. 27, 2015, which is entitled to priority under 35 U.S.C. § 119 (e) to U.S. Provisional Patent Application No. 61/971,092, filed Mar. 27, 2014, each of which application is hereby incorporated herein by reference in its entirety.

STATEMENT REGARDING FEDERALLY SPONSORED RESEARCH OR DEVELOPMENT

This invention was made with government support under U54 HD052668-01 awarded by the National Institutes of Health (NIH). The government has certain rights in the invention.

BACKGROUND OF THE INVENTION

Endometriosis, defined as the proliferation of endometrial tissue outside the uterine cavity, is one of the most common gynecologic disorders. This disease is present in approximately 10% of all reproductive-aged women, and its prevalence increases to 20% to 50% in infertile women (Taylor et al., 2002, Ann NY Acad Sci, 955: 89-100). Despite the high prevalence of the disease, the diagnosis of endometriosis is often delayed because of the complexity of the pathogenesis and diversity of symptoms (Husby et al., 2003, Acta Obstet Gynecol Scand, 82: 649-653; Dunselman et al., 2014, Hum Reprod, 29: 400-412). Although multivariate analysis of several biomarkers validated in an independent population seems promising (Vodolazkaia et al., 2012, Hum Reprod, 27: 2698-2711) there is no definite diagnostic biomarker yet available.

Imaging techniques such as ultrasound and magnetic resonance imaging do offer some benefit in the diagnosis of ovarian endometriomas, but these modalities have been shown to be unreliable in the diagnosis or staging of the more common peritoneal disease (Dunselman et al., 2014, Hum Reprod, 29: 400-412). Therefore, the direct visualization of lesions and histologic confirmation through surgical procedures are currently employed for the definitive diagnosis of endometriosis. Although laparoscopy is a minimally invasive procedure, it requires general anesthesia and developed surgical skills, and it has a high procedural cost. Additionally, laparoscopy is associated with the risk of potential intraoperative or postoperative complications.

MicroRNAs (miRNAs) are a family of endogenous, small (approximately 22 nucleotides in length), noncoding, functional RNAs, and these sequences control gene expression either by translational repression or degradation of messenger RNA transcripts after targeting the 3'-untranslated region (3'-UTR). Increasing evidence suggests that miRNAs are pivotal regulators of development and cellular homeostasis through their control of diverse biologic processes. Numerous studies have shown that aberrant miRNA expression is associated with several human diseases such as cancer, cardiovascular disorders, and inflammatory diseases as well as with gynecologic pathology (Iorio et al., 2005, Cancer Res, 65: 7065-7070; Akao et al., 2007, DNA Cell Biol, 26: 311-320; Yang et al., 2008, Cancer Res, 68: 425-433; Small et al., 2011, Nature, 469: 336-342; Brest et al., 2011, Nat Genet, 43: 242-245; Yang et al., 2008, Cancer Res, 68: 10307-10314; Marsh et al., 2008, Fertil Steril, 89: 1771-1776). Recently, the presence of circulating miRNAs was demonstrated in the blood (Mitchell et al., 2008, Proc Natl Acad Sci USA, 105: 10513-10518). Since their first description as potential diagnostic biomarkers for diffuse large B-cell lymphoma (Lawrie et al., 2008, Br J Haematol, 141: 672-675), it has been demonstrated that circulating miRNAs may be used as noninvasive biomarkers for other conditions, including autoimmune disease, sepsis, and myocardial infarction (Nakasa et al., 2008, Arthritis Rheum, 58: 1284-1292; Wang et al., 2010, Biochem Biophys Res Commun, 394: 184-188; D'Alessandra et al., 2010, Eur Heart J, 31: 2765-2773). Although the exact origin of the changes in circulating miRNA profiles is not fully understood, it has been shown that there are strong correlations between the miRNA profiles of serum/plasma and cancer tissues, suggesting that miRNAs may be released from tissues and shed into the circulation (Resnick et al., 2009, Gynecol Oncol, 112: 55-59; Wang et al., 2010, Gynecol Oncol, 119: 586-593).

MiRNAs and their target messenger RNAs (mRNAs) are expressed in endometrium and differentially expressed in endometriosis (Grechukhina et al., 2012, EMBO Mol Med, 4: 206-217; Teague et al., 2009, Mol Endocrinol, 23: 265-275; Pan et al., 2007, Mol Hum Reprod, 13: 797-806; Petracco et al., 2011, J Clin Endocrinol Metab, 96: E1925-E1933; Ramon et al., 2011, Hum Reprod, 26: 1082-1090). The differential expression of miRNA in the eutopic endometrium of women with and without endometriosis and in eutopic and ectopic endometrial samples from endometriosis patients has been identified using microarray profiling (Teague et al., 2009, Mol Endocrinol, 23: 265-275; Pan et al., 2007, Mol Hum Reprod, 13: 797-806; Ramon et al., 2011, Hum Reprod, 26: 1082-1090; Dai et al., 2012, Mol Hum Reprod, 18: 136-145). MiRNAs likely act as potent regulators of gene expression in the pathogenesis of endometriosis and endometriosis-associated infertility (Teague et al., 2010, Hum Reprod Update, 16: 142-165).

Development of new noninvasive diagnostic markers for endometriosis is crucial for early diagnosis and proper treatment and management of the disease. The present invention addresses this unmet need in the art.

SUMMARY OF THE INVENTION

The invention provides a noninvasive method of diagnosing endometriosis in a subject. In one embodiment, the method comprises a) obtaining a biological sample from the subject, b) determining the level of at least one miRNA in the biological sample, c) comparing the level of the at least one miRNA in the biological sample with the level of the at least one miRNA in a comparator, wherein when the level of the at least one miRNA in the biological sample is different than the level of the at least one miRNA in the comparator, the subject is diagnosed with endometriosis. In one embodiment, the method further comprises the step of treating the subject for endometriosis.

In one embodiment, the at least one miRNA is at least one selected from the group consisting of let-7a, let-7b, let-7c, let-7d, let-7e, let-7f, mir135a, and mir135b.

In one embodiment, the at least one miRNA is the combination of let-7b, let-7d and let-7f.

In one embodiment, the subject is human.

In one embodiment, the comparator is at least one comparator selected from the group consisting of a positive control, a negative control, a normal control, a wild-type control, a historical control, and a historical norm.

In one embodiment, the level of the at least one miRNA is lower than the level of the at least one miRNA in the comparator by at least 10%, by at least 20%, by at least 30%, by at least 40%, by at least 50%, by at least 60%, by at least 70%, by at least 80%, by at least 90%, or by at least 100%.

In one embodiment, determining the level of the at least one miRNA utilizes at least one technique selected from the group consisting of reverse transcription, PCR, and a microarray.

In one embodiment, the biological sample is selected from the group consisting of blood, serum, any a combination thereof.

The invention also provides a noninvasive method of diagnosing or providing a prognosis for endometriosis in a subject, the method comprising the step of: detecting in a biological sample altered expression of at least one gene selected from the group consisting of let-7a, let-7b, let-7c, let-7d, let-7e, let-7f, mir135a, and mir135b in a subject suspected of or having endometriosis.

In one embodiment, the at least one gene is the combination of let-7b, let-7d, and let-7f.

In one embodiment, the biological sample is selected from the group consisting of blood, serum, any a combination thereof.

The invention also provides a kit comprising a reagent that selectively binds to at least one miRNA, wherein the at least one miRNA is at least one selected from the group consisting of let-7a, let-7b, let-7c, let-7d, let-7e, let-7f, mir135a, and mir135b.

In one embodiment, the kit comprises at least three reagents, wherein the first reagent selectively binds to let-7b, wherein the second reagent binds to let-7d, and wherein the third reagent binds to let-7f.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIGS. 1A through 1D, is a series of images demonstrating that microRNAs differentially expressed in the sera of endometriosis patients and controls. The expression levels of let-7b (FIG. 1A) and mir-135a (FIG. 1D) were statistically significantly lower in patients with endometriosis than in controls, and let-7d (FIG. 1B) and let-7f (FIG. 1C) showed a trend toward decreased expression. Data are represented by box-and-whisker plots. Boxes indicate the 25th and 75th percentiles, with a solid line within the box showing the median value.

FIGS. 2A through 2F, is a series of images show the expression levels of miRNA in serum from endometriosis patients and controls according to the menstrual cycle. During the proliferative phase, (FIG. 2A) let-7b, (FIG. 2B) let-7c, (FIG. 2C) let-7d, and (FIG. 2D) let-7e were statistically significantly down-regulated in endometriosis patients compared with controls. (FIG. 2E) The expression levels of let-7f showed a trend toward down-regulation. (FIG. 2F) During the secretory phase, mir-135a was statistically significantly down-regulated in patients with endometriosis compared with controls. Data are represented by box-and-whisker plots. Boxes indicate the 25th and 75th percentiles, with a solid line within the box showing the median value.

FIGS. 3A and 3B, is a series of images showing receiver operating characteristic (ROC) curves of different miRNAs during the proliferative phase. (FIG. 3A) Let-7d showed the highest AUC of 0.905. (FIG. 3B) When the combination of the serum miRNA expression levels during the proliferative phase was used with a logistic regression model, the combination of serum let-7b, let-7d, and let-7f showed the highest AUC value of 0.929.

DETAILED DESCRIPTION

Figure 1:
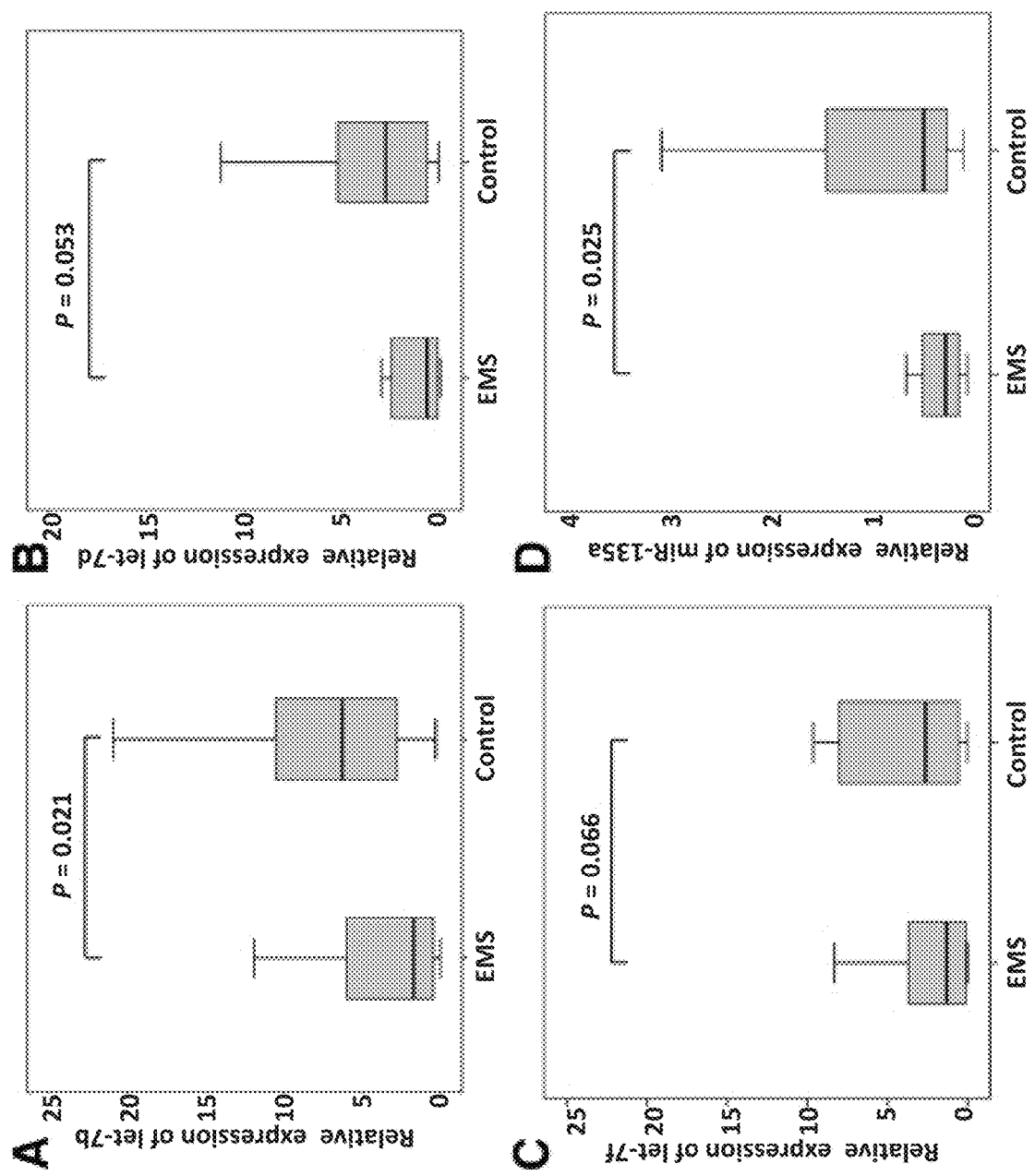
FIG. 1, comprising

The present invention relates to the discovery that the expression level of some microRNAs (miRNAs) is associated with endometriosis, preferably endometriosis during the proliferative phase. Thus, in various embodiments described herein, the methods of the invention relate to methods of diagnosing a subject as having endometriosis pain, methods of assessing a subject's risk of having or developing endometriosis, methods of assessing the severity of a subject's endometriosis, and methods of stratifying a subject having endometriosis for assignment in a clinical trial. Thus, the invention relates to compositions and methods useful for the detection and quantification of miRNAs for the diagnosis, assessment, and characterization of endometriosis in a subject in need thereof, based upon the expression level of at least one miRNA that is associated with endometriosis.

In one embodiment, the miRNAs that are associated with endometriosis is considered to be a marker or biomarker for endometriosis. In one embodiment, the biomarkers of the invention include one or more of let-7a, let-7b, let-7c, let-7d, let-7e, let-7f, mir135a, and mir135b. In another embodiment, the biomarkers of the invention include the combination of let-7b, let-7d, and let-7f.

In one embodiment, the invention provides a marker that predicts an individual's risk of developing endometriosis. In one embodiment, the markers of the invention can predict risk at a time when a prophylactic therapy can be administered such that the emergence of the disease is prevented.

In one embodiment, the markers of the invention are noninvasive biomarkers for endometriosis that allows for early detection of the disease without surgical procedures. For example, altered expression of specific miRNAs in sera of patients with endometriosis may correlate with other clinical parameters, such as pelvic pain, infertility, and disease recurrence. Therefore, the markers of the invention can be used, not only as novel biomarker for the disease, but also as markers for prognosis and recurrence. This is an advantage because repeated surgical procedures used in the art for diagnosing endometriosis and related complications can be avoided.

The present invention provides biomarkers for the diagnosis and prognosis of endometriosis. Generally, the methods of this invention find use in diagnosing or for providing a prognosis for endometriosis by detecting the expression levels of biomarkers, which are differentially expressed (up- or down-regulated) in blood or serum from a patient. Similarly, these markers can be used to diagnose reduced fertility in a patient with endometriosis or to provide a prognosis for a fertility trial in a patient suffering from endometriosis. The present invention also provides methods of identifying a compound for treating or preventing endometriosis. The present invention provides kits for the diagnosis or prognosis of endometriosis.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

"Antisense," as used herein, refers to a nucleic acid sequence which is complementary to a target sequence, such as, by way of example, complementary to a target miRNA sequence, including, but not limited to, a mature target miRNA sequence, or a sub-sequence thereof. Typically, an antisense sequence is fully complementary to the target sequence across the full length of the antisense nucleic acid sequence.

The term "body fluid" or "bodily fluid" as used herein refers to any fluid from the body of an animal. Examples of body fluids include, but are not limited to, plasma, serum, blood, lymphatic fluid, cerebrospinal fluid, synovial fluid, urine, saliva, mucous, phlegm and sputum. A body fluid sample may be collected by any suitable method. The body fluid sample may be used immediately or may be stored for later use. Any suitable storage method known in the art may be used to store the body fluid sample: for example, the sample may be frozen at about −20° C. to about −70° C. Suitable body fluids are acellular fluids. "Acellular" fluids include body fluid samples in which cells are absent or are present in such low amounts that the miRNA level determined reflects its level in the liquid portion of the sample, rather than in the cellular portion. Such acellular body fluids are generally produced by processing a cell-containing body fluid by, for example, centrifugation or filtration, to remove the cells. Typically, an acellular body fluid contains no intact cells however, some may contain cell fragments or cellular debris. Examples of acellular fluids include plasma or serum, or body fluids from which cells have been removed.

The term "clinical factors" as used herein, refers to any data that a medical practitioner may consider in determining a diagnosis or prognosis of disease. Such factors include, but are not limited to, the patient's medical history, a physical examination of the patient, complete blood count, analysis of the activity of enzymes, examination of cells, cytogenetics, and immunophenotyping of blood cells.

"Complementary" as used herein refers to the broad concept of subunit sequence complementarity between two nucleic acids. When a nucleotide position in both of the molecules is occupied by nucleotides normally capable of base pairing with each other, then the nucleic acids are considered to be complementary to each other at this position. Thus, two nucleic acids are substantially complementary to each other when at least about 50%, preferably at least about 60% and more preferably at least about 80% of corresponding positions in each of the molecules are occupied by nucleotides which normally base pair with each other (e.g., A:T and G:C nucleotide pairs).

As used herein, the term "diagnosis" means detecting a disease or disorder or determining the stage or degree of a disease or disorder. Usually, a diagnosis of a disease or disorder is based on the evaluation of one or more factors and/or symptoms that are indicative of the disease. That is, a diagnosis can be made based on the presence, absence or amount of a factor which is indicative of presence or absence of the disease or condition. Each factor or symptom that is considered to be indicative for the diagnosis of a particular disease does not need be exclusively related to the particular disease; i.e. there may be differential diagnoses that can be inferred from a diagnostic factor or symptom. Likewise, there may be instances where a factor or symptom that is indicative of a particular disease is present in an individual that does not have the particular disease. The diagnostic methods may be used independently, or in combination with other diagnosing and/or staging methods known in the medical art for a particular disease or disorder.

As used herein, the phrase "difference of the level" refers to differences in the quantity of a particular marker, such as a nucleic acid or a protein, in a sample as compared to a control or reference level. For example, the quantity of a particular biomarker may be present at an elevated amount or at a decreased amount in samples of patients with a disease compared to a reference level. In one embodiment, a "difference of a level" may be a difference between the quantity of a particular biomarker present in a sample as compared to a control of at least about 1%, at least about 2%, at least about 3%, at least about 5%, at least about 10%, at least about 15%, at least about 20%, at least about 25%, at least about 30%, at least about 35%, at least about 40%, at least about 50%, at least about 60%, at least about 75%, at least about 80% or more. In one embodiment, a "difference of a level" may be a statistically significant difference between the quantity of a biomarker present in a sample as compared to a control. For example, a difference may be statistically significant if the measured level of the biomarker falls outside of about 1.0 standard deviations, about 1.5 standard deviations, about 2.0 standard deviations, or about 2.5 stand deviations of the mean of any control or reference group.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

The term "control or reference standard" describes a material comprising none, or a normal, low, or high level of one of more of the marker (or biomarker) expression products of one or more the markers (or biomarkers) of the invention, such that the control or reference standard may serve as a comparator against which a sample can be compared.

The terms "dysregulated" and "dysregulation" as used herein describes a decreased (down-regulated) or increased (up-regulated) level of expression of a miRNA present and detected in a sample obtained from subject as compared to the level of expression of that miRNA in a comparator sample, such as a comparator sample obtained from one or more normal, not-at-risk subjects, or from the same subject at a different time point. In some instances, the level of miRNA expression is compared with an average value obtained from more than one not-at-risk individuals. In other instances, the level of miRNA expression is compared with a miRNA level assessed in a sample obtained from one normal, not-at-risk subject.

By the phrase "determining the level of marker (or biomarker) expression" is meant an assessment of the degree of expression of a marker in a sample at the nucleic acid or protein level, using technology available to the skilled artisan to detect a sufficient portion of any marker expression product.

The terms "determining," "measuring," "assessing," and "assaying" are used interchangeably and include both quantitative and qualitative measurement, and include determining if a characteristic, trait, or feature is present or not. Assessing may be relative or absolute. "Assessing the presence of" includes determining the amount of something present, as well as determining whether it is present or absent.

"Differentially increased expression" or "up regulation" refers to expression levels which are at least 10% or more, for example, 20%, 30%, 40%, or 50%, 60%, 70%, 80%, 90% higher or more, and/or 1.1 fold, 1.2 fold, 1.4 fold, 1.6 fold, 1.8 fold, 2.0 fold higher or more, and any and all whole or partial increments there between than a comparator.

"Differentially decreased expression" or "down regulation" refers to expression levels which are at least 10% or more, for example, 20%, 30%, 40%, or 50%, 60%, 70%, 80%, 90% lower or less, and/or 2.0 fold, 1.8 fold, 1.6 fold, 1.4 fold, 1.2 fold, 1.1 fold or less lower, and any and all whole or partial increments there between than a comparator.

As used herein "endogenous" refers to any material from or produced inside an organism, cell, tissue or system.

The term "expression" as used herein is defined as the transcription and/or translation of a particular nucleotide sequence.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 5'-ATTGCC-3' and 5'-TATGGC-3' share 50% homology.

As used herein, "homology" is used synonymously with "identity."

"Inhibitors," "activators," and "modulators" of the markers are used to refer to activating, inhibitory, or modulating molecules identified using in vitro and in vivo assays of endometriosis biomarkers. Inhibitors are compounds that, e.g., bind to, partially or totally block activity, decrease, prevent, delay activation, inactivate, desensitize, or down regulate the activity or expression of endometriosis biomarkers. "Activators" are compounds that increase, open, activate, facilitate, enhance activation, sensitize, agonize, or up regulate activity of endometriosis biomarkers, e.g., agonists Inhibitors, activators, or modulators also include genetically modified versions of endometriosis biomarkers, e.g., versions with altered activity, as well as naturally occurring and synthetic ligands, antagonists, agonists, antibodies, peptides, cyclic peptides, nucleic acids, antisense molecules, ribozymes, RNAi, microRNA, and siRNA molecules, small organic molecules and the like. Such assays for inhibitors and activators include, e.g., expressing endometriosis biomarkers in vitro, in cells, or cell extracts, applying putative modulator compounds, and then determining the functional effects on activity, as described elsewhere herein.

As used herein, an "instructional material" includes a publication, a recording, a diagram, or any other medium of expression which can be used to communicate the usefulness of a compound, composition, vector, method or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

As used herein, "isolated" means altered or removed from the natural state through the actions, directly or indirectly, of a human being. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

"Measuring" or "measurement," or alternatively "detecting" or "detection," means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's clinical parameters.

As used herein, "microRNA" or "miRNA" describes small non-coding RNA molecules, generally about 15 to about 50 nucleotides in length, preferably 17-23 nucleotides, which can play a role in regulating gene expression through, for example, a process termed RNA interference (RNAi). RNAi describes a phenomenon whereby the presence of an RNA sequence that is complementary or antisense to a sequence in a target gene messenger RNA (mRNA) results in inhibition of expression of the target gene. miRNAs are processed from hairpin precursors of about 70 or more nucleotides (pre-miRNA) which are derived from primary transcripts (pri-miRNA) through sequential cleavage by RNAse III enzymes. miRBase is a comprehensive microRNA database located at www.mirbase.org, incorporated by reference herein in its entirety for all purposes.

A "mutation," as used herein, refers to a change in nucleic acid or polypeptide sequence relative to a reference sequence (which is preferably a naturally-occurring normal or "wild-type" sequence), and includes translocations, deletions, insertions, and substitutions/point mutations. A "mutant," as used herein, refers to either a nucleic acid or protein comprising a mutation.

"Naturally occurring" as used herein describes a composition that can be found in nature as distinct from being artificially produced. For example, a nucleotide sequence present in an organism, which can be isolated from a source in nature and which has not been intentionally modified by a person, is naturally occurring.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand." Sequences on the DNA strand which are located 5' to a reference point on the DNA are referred to as "upstream sequences." Sequences on the DNA strand which are 3' to a reference point on the DNA are referred to as "downstream sequences."

As used herein, "polynucleotide" includes cDNA, RNA, DNA/RNA hybrid, anti-sense RNA, siRNA, miRNA, genomic DNA, synthetic forms, and mixed polymers, both sense and antisense strands, and may be chemically or biochemically modified to contain non-natural or derivatized, synthetic, or semi-synthetic nucleotide bases. Also, included within the scope of the invention are alterations of a wild type or synthetic gene, including but not limited to deletion, insertion, substitution of one or more nucleotides, or fusion to other polynucleotide sequences.

As used herein, a "primer" for amplification is an oligonucleotide that specifically anneals to a target or marker nucleotide sequence. The 3' nucleotide of the primer should be identical to the target or marker sequence at a corresponding nucleotide position for optimal primer extension by a polymerase. As used herein, a "forward primer" is a primer that anneals to the anti-sense strand of double stranded DNA (dsDNA). A "reverse primer" anneals to the sense-strand of dsDNA.

The term "recombinant DNA" as used herein is defined as DNA produced by joining pieces of DNA from different sources.

As used herein, the term "providing a prognosis" refers to providing a prediction of the probable course and outcome of endometriosis, including prediction of severity, duration, chances of recovery, etc. The methods can also be used to devise a suitable therapeutic plan, e.g., by indicating whether or not the condition is still at an early stage or if the condition has advanced to a stage where aggressive therapy would be ineffective.

A "reference level" of a biomarker means a level of the biomarker that is indicative of a particular disease state, phenotype, or lack thereof, as well as combinations of disease states, phenotypes, or lack thereof. A "positive" reference level of a biomarker means a level that is indicative of a particular disease state or phenotype. A "negative" reference level of a biomarker means a level that is indicative of a lack of a particular disease state or phenotype.

"Sample" or "biological sample" as used herein means a biological material isolated from an individual. The biological sample may contain any biological material suitable for detecting the desired biomarkers, and may comprise cellular and/or non-cellular material obtained from the individual.

"Standard control value" as used herein refers to a predetermined amount of a particular protein or nucleic acid that is detectable in a biological sample. The standard control value is suitable for the use of a method of the present invention, in order for comparing the amount of a protein or nucleic acid of interest that is present in a biological sample. An established sample serving as a standard control provides an average amount of the protein or nucleic acid of interest in the biological sample that is typical for an average, healthy person of reasonably matched background, e.g., gender, age, ethnicity, and medical history. A standard control value may vary depending on the protein or nucleic acid of interest and the nature of the sample (e.g., serum).

The terms "subject," "patient," "individual," and the like are used interchangeably herein, and refer to any animal, or cells thereof whether in vitro or in situ, amenable to the methods described herein. In certain non-limiting embodiments, the patient, subject or individual is a human.

The terms "underexpress", "underexpression", "underexpressed", or "down-regulated" interchangeably refer to a protein or nucleic acid that is transcribed or translated at a detectably lower level in a biological sample from a woman with endometriosis, in comparison to a biological sample from a woman without endometriosis. The term includes underexpression due to transcription, post transcriptional processing, translation, post-translational processing, cellular localization (e.g., organelle, cytoplasm, nucleus, cell surface), and RNA and protein stability, as compared to a control. Underexpression can be detected using conventional techniques for detecting mRNA (i.e., Q-PCR, RT-PCR, PCR, hybridization) or proteins (i.e., ELISA, immunohistochemical techniques). Underexpression can be 10%, 20%, 30%, 40%, 50%, 60%, 70%, 80%, 90% or less in comparison to a control. In certain instances, underexpression is 1-, 2-, 3-, 4-, 5-, 6-, 7-, 8-, 9-, 10-fold or more lower levels of transcription or translation in comparison to a control.

The terms "overexpress", "overexpression", "overexpressed", or "up-regulated" interchangeably refer to a protein or nucleic acid (RNA) that is transcribed or translated at a detectably greater level, usually in a biological sample from a woman with endometriosis, in comparison to a biological sample from a woman without endometriosis. The term includes overexpression due to transcription, post transcriptional processing, translation, post-translational processing, cellular localization (e.g., organelle, cytoplasm, nucleus, cell surface), and RNA and protein stability, as compared to a cell from a woman without endometriosis. Overexpression can be detected using conventional techniques for detecting mRNA (i.e., Q-PCR, RT-PCR, PCR, hybridization) or proteins (i.e., ELISA, immunohistochemical techniques). Overexpression can be 10%, 20%, 30%, 40%, 50%, 60%, 70%, 80%, 90% or more in comparison to a cell from a woman without endometriosis. In certain instances, overexpression is 1-, 2-, 3-, 4-, 5-, 6-, 7-, 8-, 9-, 10-fold, or more higher levels of transcription or translation in comparison to a cell from a woman without endometriosis.

"Variant" as the term is used herein, is a nucleic acid sequence or a peptide sequence that differs in sequence from a reference nucleic acid sequence or peptide sequence respectively, but retains essential properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

In one aspect, the present invention relates to the discovery of a link between alterations in circulating miRNA levels and endometriosis. In some embodiments, the level of circulating miRNAs, alone and in combination with conventional endometriosis serum markers, are used to improve endometriosis detection. In exemplary embodiments, the miRNAs are selected from the group consisting of: let-7a, let-7b, let-7c, let-7d, let-7e, let-7f, mir135a, mir135b, and any combination thereof.

In one aspect, the methods generally provide for the detection, measuring, and comparison of a pattern of circulating miRNA in a patient sample. In the context of endometriosis, it is frequently difficult to have access to the diseased cells. In various embodiments, the present methods overcome problems of cancer diagnosis by determining the levels of miRNAs in the plasma of patients with liver diseases. An alteration (i.e., an increase or decrease) in the level of a miRNA gene product in the sample obtained from the subject, relative to the level of a corresponding miRNA gene product in a control sample, is indicative of the presence of endometriosis in the subject. In one embodiment, the level of at least one miRNA gene product in the test sample is greater than the level of the corresponding miRNA gene product in the control sample. In another embodiment, the level of at least one miRNA gene product in the test sample is less than the level of the corresponding miRNA gene product in the control sample.

Additional diagnostic markers may be combined with the circulating miRNA level to construct models for predicting the presence or absence or stage of a disease. For example, clinical factors of relevance to the diagnosis of endometriosis diseases, include, but are not limited to, the patient's medical history, a physical examination, and other biomarkers.

Generally, the methods of this invention find use in diagnosing or for providing a prognosis for endometriosis by detecting the expression levels of biomarkers, which are differentially expressed (up- or down-regulated) in blood or serum from a patient. These markers can be used to distinguish the stage or severity of endometriosis. These markers can also be used to provide a prognosis for the course of treatment in a patient with endometriosis. Similarly, these markers can be used to diagnose infertility in a patient with endometriosis or to provide a prognosis for a fertility trial in a patient suffering from endometriosis. The biomarkers of the present invention can be used alone or in combination for the diagnosis or prognosis of endometriosis.

In one embodiment, the methods of the present invention find use in assigning treatment to a patient suffering from endometriosis. By detecting the expression levels of biomarkers found herein, the appropriate treatment can be assigned to a patient suffering from endometriosis. These treatments can include, but are not limited to, hormone therapy, chemotherapy, immunotherapy, and surgical treatment. Similarly, the methods of the current invention can be used to assign treatment to a patient with reduced fertility due to endometriosis. In this fashion, by determining the degree to which the patient's fertility has been reduced, through the detection of biomarkers found herein, the appropriate treatment can be assigned. Relevant treatments include, but are not limited to, hormone therapy, chemotherapy, immunotherapy, and surgical treatment.

Diagnostic and prognostic kits comprising one or more markers for use are provided herein. Also provided by the invention are methods for identifying compounds that are able to prevent or treat endometriosis or reduced fertility caused by endometriosis by modulating the expression level or activity of markers found in any one of the identified gene subsets. Therapeutic methods are provided, wherein endometriosis or reduced fertility caused by endometriosis is treated using an agent that targets the markers of the invention.

In some embodiments, a miRNA associated with endometriosis is down-regulated, or expressed at a lower than normal level. Thus, the invention relates to compositions and methods useful for the diagnosis, assessment, and characterization of endometriosis in a subject in need thereof, based upon the expression level of at least one miRNA that is associated with endometriosis. Accordingly, the invention provides a method of treating endometriosis by targeting the miRNAs that are down-regulated in order to increase the expression of these miRNAs.

In various embodiments, the methods of the invention relate to methods of assessing a subject's risk of having or developing endometriosis, methods of assessing the severity of a subject's endometriosis, methods of diagnosing endometriosis, methods of characterizing endometriosis, and methods of stratifying a subject having endometriosis in a clinical trial.

In various embodiments of the compositions and methods of the invention described herein, the miRNA associated with endometriosis is at least one of let-7 miRNAs. Lethal-7 (let-7) is a founding member of the miRNA family in *C. elegans*. Human orthologs include let-7a, let-7b, let-7c, let-7d, let-7e, let-7f, let-7g, and let-7i. Sequences of let-7 family members are publicly available from miRBase at (www.mirbase.org). Exemplary let-7 miRNAs include, but are not limited to, let-7a (let-7a-1, let-7a-2, let-7a-3), let-7b, let-7c, let-7d, let-7e, let-7f (let-7f-1 and let-7f-2), let-7g, and let-7i. For the following sequences, thymine (T) may be substituted for uracil (U). let-7a comprises the sequence UUGAUAUGUUGGAUGAUGGAGU (SEQ ID NO: 1). let-7b comprises the sequence UUGGUGUGUUG-GAUGAUGGAGU (SEQ ID NO: 2). let-7c comprises the sequence UUGGUAUGUUGGAUGAUGGAGU (SEQ ID NO: 3). let-7d comprises the sequence UGAUACGUUG-GAUGAUGGAGA (SEQ ID NO: 4). let-7e comprises the sequence UAUAUGUUGGAGGAUGGAGU (SEQ ID NO: 5). let-7f comprises the sequence UUGAUAUGUUA-GAUGAUGGAGU (SEQ ID NO: 6). let-7g comprises the sequence GACAUGUUUGAUGAUGGAGU (SEQ ID NO: 7). let-7i comprises the sequence UGUCGUGUUU-GUUGAUGGAGU (SEQ ID NO: 8).

In one embodiment, the biomarkers of the invention include one or more of let-7a, let-7b, let-7c, let-7d, let-7e, let-7f, mir135a, and mir135b. In one embodiment, biomarkers of the invention useful for diagnosing endometriosis include one or more of let-7b, let-7c, let-7d, let-7e, and let-7f. In a preferred embodiment, biomarkers of the invention useful for diagnosing endometriosis include the combination of let-7b, let-7d and let-7f.

Accordingly, the invention provides a new and convenient platform for detecting a marker of endometriosis. In one embodiment, the system of the invention provides a platform for detecting a marker of endometriosis with at least 80% sensitivity, preferably at least 90%, preferably at least 91%, preferably at least 92%, preferably at least 93%, preferably at least 94%, preferably at least 95%, preferably at least 96%, preferably at least 97%, preferably at least 98%, preferably at least 99%, preferably at least 100%.

In one embodiment, the system of the invention provides a platform for detecting a marker of endometriosis. In one embodiment, the system of the invention provides a platform for detecting a marker of endometriosis with at least 80% specificity, preferably at least 90%, preferably at least 91%, preferably at least 92%, preferably at least 93%, preferably at least 94%, preferably at least 95%, preferably at least 96%, preferably at least 97%, preferably at least 98%, preferably at least 99%, preferably at least 100%.

In one embodiment, the invention provides a system for detecting a marker of endometriosis, with at least 90%, 91%, 92%, 93%, 94%, 95%, 96%, 97%, 98%, 99%, 100% sensitivity; at least 90%, 91%, 92%, 93%, 94%, 95%, 96%, 97%, 98%, 99%, 100% specificity; or both at least 90%, 91%, 92%, 93%, 94%, 95%, 96%, 97%, 98%, 99%, 100% sensitivity and specificity. In one embodiment, the invention provides a system for detecting a marker of endometriosis with at least 90%, 91%, 92%, 93%, 94%, 95%, 96%, 97%, 98%, 99%, 100% accuracy.

Sample Preparation

Test samples of acellular body fluid or cell-containing samples may be obtained from an individual or patient. Methods of obtaining test samples are well-known to those of skill in the art and include, but are not limited to aspirations or drawing of blood or other fluids. Samples may include, but are not limited to, whole blood, serum, plasma, saliva, cerebrospinal fluid (CSF), pericardial fluid, pleural fluid, urine, and eye fluid. In some embodiments in which the test sample contains cells, the cells may be removed from the liquid portion of the sample by methods known in the art (e.g., centrifugation) to yield acellular body fluid. In suitable embodiments, serum or plasma are used as the acellular body fluid sample. Plasma and serum can be prepared from whole blood using suitable methods well-known in the art. In these embodiments, data may be normalized by volume of acellular body fluid.

Variability in sample preparation of cell-containing samples can be corrected by normalizing the data by, for example, protein content or cell number. In certain embodiments, the sample may be normalized relative to the total protein content in the sample. Total protein content in the sample can be determined using standard procedures, including, without limitation, Bradford assay and the Lowry method. In other embodiments, the sample may be normalized relative to cell number.

Assays

The present invention relates to the discovery that the expression level of particular miRNAs is associated with the presence, development, progression and severity of endometriosis. In various embodiments, the invention relates to a genetic screening assay of a subject to determine the level of expression of at least one miRNA associated with endometriosis in the subject. The present invention provides methods of assessing level of at least one miRNA associated with endometriosis, as well as methods of diagnosing a subject as having, or as being at risk of developing, endometriosis based upon the level of expression of at least one miRNA associated with endometriosis. In some embodiments, the diagnostic assays described herein are in vitro assays.

In one embodiment, the method of the invention is a diagnostic assay for assessing the presence, development, progression and severity of endometriosis in a subject in need thereof, by determining whether the level of at least one miRNA associated with endometriosis is decreased in a biological sample obtained from the subject. In various embodiments, to determine whether the level of the at least one miRNA associated with endometriosis is decreased in a biological sample obtained from the subject, the level of the at least one miRNA is compared with the level of at least one comparator control, such as a positive control, a negative control, a normal control, a wild-type control, a historical control, a historical norm, or the level of another reference molecule in the biological sample. In some embodiments, the diagnostic assay of the invention is an in vitro assay. In other embodiments, the diagnostic assay of the invention is an in vivo assay. The miRNA identified by the assay can be any miRNA that is associated with endometriosis. In some embodiments, the miRNA is at least one of let-7a, let-7b, let-7c, let-7d, let-7e, let-7f, mir135a, and mir135b. In various embodiments of the invention, the at least one miRNA associated with endometriosis is at least two miRNAs, at least three miRNAs, at least four miRNAs, at least five miRNAs, at least six miRNAs, at least seven miRNAs, at least eight miRNAs. The results of the diagnostic assay can be used alone, or in combination with other information from the subject, or other information from the biological sample obtained from the subject.

In various embodiments of the assays of the invention, the level of the at least one miRNA associated with endometriosis is determined to be down-regulated when the level of the at least one miRNA is decreased by at least 10%, by at least 20%, by at least 30%, by at least 40%, by at least 50%, by at least 60%, by at least 70%, by at least 80%, by at least 90%, by at least 100%, by at least 125%, by at least 150%, by at least 175%, by at least 200%, by at least 250%, by at least 300%, by at least 400%, by at least 500%, by at least 600%, by at least 700%, by at least 800%, by at least 900%, by at least 1000%, by at least 1500%, by at least 2000%, or by at least 5000%, when compared with a comparator control.

In the assay methods of the invention, a test biological sample from a subject is assessed for the expression level of at least one miRNA associated with endometriosis. The test biological sample can be an in vitro sample or an in vivo sample. In various embodiments, the subject is a human subject, and may be of any race, sex and age. Representative subjects include those who are suspected of having endometriosis, those who have been diagnosed with endometriosis, those whose have endometriosis, those who have had endometriosis, those who at risk of a recurrence of endometriosis, and those who are at risk of developing endometriosis.

In some embodiments, an endometriosis associated miRNA-binding molecule is used in vivo for the diagnosis of endometriosis. In some embodiments, the endometriosis associated miRNA-binding molecule is nucleic acid that hybridizes with an endometriosis associated miRNA of the invention.

In one embodiment, the test sample is a sample containing at least a fragment of a nucleic acid comprising a miRNA associated with endometriosis. The term, "fragment," as used herein, indicates that the portion of a nucleic acid (e.g., DNA, mRNA or cDNA) that is sufficient to identify it as comprising a miRNA associated with endometriosis.

In some embodiments, the test sample is prepared from a biological sample obtained from the subject. The biological sample can be a sample from any source which contains a nucleic acid comprising endometriosis associated miRNA, such as a body fluid (e.g., blood, plasma, serum, saliva, urine, etc.), or a tissue, or an exosome, or a cell, or a combination thereof. A biological sample can be obtained by appropriate methods, such as, by way of examples, biopsy or fluid draw. The biological sample can be used as the test sample; alternatively, the biological sample can be processed to enhance access to polypeptides, nucleic acids, or copies of nucleic acids (e.g., copies of nucleic acids comprising a miRNA associated with endometriosis), and the processed biological sample can then be used as the test sample. For example, in various embodiments, nucleic acid is prepared from a biological sample, for use in the methods. Alternatively or in addition, if desired, an amplification method can be used to amplify nucleic acids comprising all or a fragment of a nucleic acid in a biological sample, for use as the test sample in the assessment of the expression level of a miRNA associated with endometriosis.

The test sample is assessed to determine the level of expression of at least one miRNA associated with endometriosis present in the nucleic acid of the subject. In general, detecting a miRNA may be carried out by determining the presence or absence of a nucleic acid containing a miRNA of interest in the test sample.

In some embodiments, hybridization methods, such as Northern analysis, or in situ hybridizations, can be used (see Current Protocols in Molecular Biology, 2012, Ausubel, F. et al., eds., John Wiley & Sons, including all supplements). For example, the presence of a miRNA associated with endometriosis can be indicated by hybridization to a nucleic acid probe. A "nucleic acid probe," as used herein, can be a nucleic acid probe, such as a DNA probe or an RNA probe. For representative examples of use of nucleic acid probes, see, for example, U.S. Pat. Nos. 5,288,611 and 4,851,330.

To detect at least one miRNA of interest, a hybridization sample is formed by contacting the test sample with at least one nucleic acid probe. A preferred probe for detecting miRNA is a labeled nucleic acid probe capable of hybridizing to miRNA. The nucleic acid probe can be, for example, a full-length nucleic acid molecule, or a portion thereof, such as an oligonucleotide of at least 10, 15, or 25 nucleotides in length and sufficient to specifically hybridize under stringent conditions to appropriate miRNA. The hybridization sample is maintained under conditions which are sufficient to allow specific hybridization of the nucleic acid probe to a miRNA target of interest. Specific hybridization can be performed under high stringency conditions or moderate stringency conditions, as appropriate. In a preferred embodiment, the hybridization conditions for specific hybridization are high stringency. Specific hybridization, if present, is then detected using standard methods. If specific hybridization occurs between the nucleic acid probe and a miRNA in the test sample, the sequence that is present in the nucleic acid probe is also present in the miRNA of the subject. More than one nucleic acid probe can also be used concurrently in this method. Specific hybridization of any one of the nucleic acid probes is indicative of the presence of the miRNA of interest, as described herein.

Alternatively, a peptide nucleic acid (PNA) probe can be used instead of a nucleic acid probe in the hybridization methods described herein. PNA is a DNA mimic having a peptide-like, inorganic backbone, such as N-(2-aminoethyl) glycine units, with an organic base (A, G, C, T or U) attached to the glycine nitrogen via a methylene carbonyl linker (see, for example, 1994, Nielsen et al., Bioconjugate Chemistry 5:1). The PNA probe can be designed to specifically hybridize to a nucleic acid sequence comprising at least one miRNA of interest. Hybridization of the PNA probe to a nucleic acid sequence is indicative of the presence of a miRNA of interest.

Direct sequence analysis can also be used to detect miRNAs of interest. A sample comprising nucleic acid can be used, and PCR or other appropriate methods can be used to amplify all or a fragment of the nucleic acid, and/or its flanking sequences, if desired.

In another embodiment, arrays of oligonucleotide probes that are complementary to target nucleic acid sequences from a subject can be used to detect, identify and quantify miRNAs associated with endometriosis. For example, in one embodiment, an oligonucleotide array can be used. Oligonucleotide arrays typically comprise a plurality of different oligonucleotide probes that are coupled to a surface of a substrate in different known locations. These oligonucleotide arrays, also known as "Genechips," have been generally described in the art, for example, U.S. Pat. No. 5,143,854 and PCT patent publication Nos. WO 90/15070 and 92/10092. These arrays can generally be produced using mechanical synthesis methods or light directed synthesis methods which incorporate a combination of photolithographic methods and solid phase oligonucleotide synthesis methods. See Fodor et al., Science, 251:767-777 (1991), Pirrung et al., U.S. Pat. No. 5,143,854 (see also PCT Application No. WO 90/15070) and Fodor et al., PCT Publication No. WO 92/10092 and U.S. Pat. No. 5,424,186. Techniques for the synthesis of these arrays using mechanical synthesis methods are described in, e.g., U.S. Pat. No. 5,384,261.

After an oligonucleotide array is prepared, a sample containing miRNA is hybridized with the array and scanned for miRNAs. Hybridization and scanning are generally carried out by methods described herein and also in, e.g., Published PCT Application Nos. WO 92/10092 and WO 95/11995, and U.S. Pat. No. 5,424,186, the entire teachings of which are incorporated by reference herein.

In brief, a target miRNA sequence is amplified by well-known amplification techniques, e.g., RT, PCR. Typically, this involves the use of primer sequences that are complementary to the target miRNA. Amplified target, generally incorporating a label, is then hybridized with the array under appropriate conditions. Upon completion of hybridization and washing of the array, the array is scanned to determine the position on the array to which the target sequence hybridizes. The hybridization data obtained from the scan is typically in the form of fluorescence intensities as a function of location on the array.

Other methods of nucleic acid analysis can be used to detect miRNAs of interest. Representative methods include direct manual sequencing (1988, Church and Gilbert, Proc. Natl. Acad. Sci. USA 81:1991-1995; 1977, Sanger et al., Proc. Natl. Acad. Sci. 74:5463-5467; Beavis et al. U.S. Pat. No. 5,288,644); automated fluorescent sequencing; single-stranded conformation polymorphism assays (SSCP); clamped denaturing gel electrophoresis (CDGE); denaturing gradient gel electrophoresis (DGGE) (Sheffield et al., 1981, Proc. Natl. Acad. Sci. USA 86:232-236), mobility shift analysis (Orita et al., 1989, Proc. Natl. Acad. Sci. USA 86:2766-2770; Rosenbaum and Reissner, 1987, Biophys. Chem. 265:1275; 1991, Keen et al., Trends Genet. 7:5); RNase protection assays (Myers, et al., 1985, Science 230: 1242); Luminex xMAP™ technology; high-throughput sequencing (HTS) (Gundry and Vijg, 2011, Mutat Res, doi:10.1016/j.mrfmmm.2011.10.001); next-generation sequencing (NGS) (Voelkerding et al., 2009, Clinical Chemistry 55:641-658; Su et al., 2011, Expert Rev Mol Diagn. 11:333-343; Ji and Myllykangas, 2011, Biotechnol Genet Eng Rev 27:135-158); and/or ion semiconductor sequencing (Rusk, 2011, Nature Methods doi:10.1038/nmeth.f.330; Rothberg et al., 2011, Nature 475:348-352). These and other methods, alone or in combination, can be used to detect and quantity of at least one miRNA of interest, in a biological sample obtained from a subject. In one embodiment of the invention, the methods of assessing a biological sample to detect and quantify a miRNA of interest, as described herein, are used to diagnose, assess and characterize endometriosis in a subject in need thereof.

The probes and primers according to the invention can be labeled directly or indirectly with a radioactive or nonradioactive compound, by methods well known to those skilled in the art, in order to obtain a detectable and/or quantifiable signal; the labeling of the primers or of the probes according to the invention is carried out with radioactive elements or with nonradioactive molecules. Among the radioactive isotopes used, mention may be made of $^{32}$P, $^{33}$P, $^{35}$S or $^{3}$H. The nonradioactive entities are selected from ligands such as biotin, avidin, streptavidin or digoxigenin, haptenes, dyes, and luminescent agents such as radioluminescent, chemoluminescent, bioluminescent, fluorescent or phosphorescent agents.

Nucleic acids can be obtained from the biological sample using known techniques. Nucleic acid herein includes RNA, including mRNA, miRNA, etc. The nucleic acid can be double-stranded or single-stranded (i.e., a sense or an antisense single strand) and can be complementary to a nucleic acid encoding a polypeptide. The nucleic acid content may also be obtained from an extraction performed on a fresh or fixed biological sample.

There are many methods known in the art for the detection of specific nucleic acid sequences and new methods are continually reported. A great majority of the known specific nucleic acid detection methods utilize nucleic acid probes in specific hybridization reactions.

In the Northern blot, the nucleic acid probe is preferably labeled with a tag. That tag can be a radioactive isotope, a fluorescent dye or the other well-known materials. Another type of process for the specific detection of nucleic acids of exogenous organisms in a body sample known in the art are the hybridization methods as exemplified by U.S. Pat. No. 6,159,693 and U.S. Pat. No. 6,270,974, and related patents. To briefly summarize one of those methods, a nucleic acid probe of at least 10 nucleotides, preferably at least 15 nucleotides, more preferably at least 25 nucleotides, having a sequence complementary to a desired region of the target nucleic acid of interest is hybridized in a sample, subjected to depolymerizing conditions, and the sample is treated with an ATP/luciferase system, which will luminesce if the nucleic sequence is present. In quantitative Northern blotting, levels of the polymorphic nucleic acid can be compared to wild-type levels of the nucleic acid.

A further process for the detection of hybridized nucleic acid takes advantage of the polymerase chain reaction (PCR). The PCR process is well known in the art (U.S. Pat. No. 4,683,195, No. 4,683,202, and U.S. Pat. No. 4,800,159). To briefly summarize PCR, nucleic acid primers, complementary to opposite strands of a nucleic acid amplification target nucleic acid sequence, are permitted to anneal to the denatured sample. A DNA polymerase (typically heat stable) extends the DNA duplex from the hybridized primer. The process is repeated to amplify the nucleic acid target. If the nucleic acid primers do not hybridize to the sample, then there is no corresponding amplified PCR product.

In PCR, the nucleic acid probe can be labeled with a tag as discussed before. Most preferably the detection of the duplex is done using at least one primer directed to the target nucleic acid. In yet another embodiment of PCR, the detection of the hybridized duplex comprises electrophoretic gel separation followed by dye-based visualization.

Nucleic acid amplification procedures by PCR are well known and are described in U.S. Pat. No. 4,683,202. Briefly, the primers anneal to the target nucleic acid at sites distinct from one another and in an opposite orientation. A primer annealed to the target sequence is extended by the enzymatic action of a heat stable polymerase. The extension product is then denatured from the target sequence by heating, and the process is repeated. Successive cycling of this procedure on both strands provides exponential amplification of the region flanked by the primers.

Amplification is then performed using a PCR-type technique, that is to say the PCR technique or any other related technique. Two primers, complementary to the target nucleic acid sequence are then added to the nucleic acid content along with a polymerase, and the polymerase amplifies the DNA region between the primers.

Stem-loop RT-PCR is a PCR method that is useful in the methods of the invention to amplify and quantify miRNAs of interest (See Caifu et al., 2005, Nucleic Acids Research 33:e179; Mestdagh et al., 2008, Nucleic Acids Research 36:e143; Varkonyi-Gasic et al., 2011, Methods Mol Biol. 744:145-57). Briefly, the method includes two steps: RT and real-time PCR. First, a stem-loop RT primer is hybridized to a miRNA molecule and then reverse transcribed with a reverse transcriptase. Then, the RT products are quantified using conventional real-time PCR.

The expression specifically hybridizing in stringent conditions refers to a hybridizing step in the process of the invention where the oligonucleotide sequences selected as probes or primers are of adequate length and sufficiently unambiguous so as to minimize the amount of non-specific binding that may occur during the amplification. The oligonucleotide probes or primers herein described may be prepared by any suitable methods such as chemical synthesis methods.

Hybridization is typically accomplished by annealing the oligonucleotide probe or primer to the template nucleic acid under conditions of stringency that prevent non-specific binding but permit binding of this template nucleic acid which has a significant level of homology with the probe or primer.

Among the conditions of stringency is the melting temperature (Tm) for the amplification step using the set of primers, which is in the range of about 50° C. to about 95° C. Typical hybridization and washing stringency conditions depend in part on the size (i.e., number of nucleotides in length) of the template nucleic acid or the oligonucleotide probe, the base composition and monovalent and divalent cation concentrations (Ausubel et al., 1994, eds Current Protocols in Molecular Biology).

In a preferred embodiment, the process for determining the quantitative and qualitative profile according to the present invention is characterized in that the amplifications are real-time amplifications performed using a labeled probe, preferably a labeled hydrolysis-probe, capable of specifically hybridizing in stringent conditions with a segment of a nucleic acid sequence, or polymorphic nucleic acid sequence. The labeled probe is capable of emitting a detectable signal every time each amplification cycle occurs.

The real-time amplification, such as real-time PCR, is well known in the art, and the various known techniques will be employed in the best way for the implementation of the present process. These techniques are performed using various categories of probes, such as hydrolysis probes, hybridization adjacent probes, or molecular beacons. The techniques employing hydrolysis probes or molecular beacons are based on the use of a fluorescence quencher/reporter system, and the hybridization adjacent probes are based on the use of fluorescence acceptor/donor molecules.

Hydrolysis probes with a fluorescence quencher/reporter system are available in the market, and are for example commercialized by the Applied Biosystems group (USA). Many fluorescent dyes may be employed, such as FAM dyes (6-carboxy-fluorescein), or any other dye phosphoramidite reagents. Among the stringent conditions applied for any one of the hydrolysis-probes of the present invention is the Tm, which is in the range of about 50° C. to 95° C. Preferably, the Tm for any one of the hydrolysis-probes of the present invention is in the range of about 55° C. to about 80° C. Most preferably, the Tm applied for any one of the hydrolysis-probes of the present invention is about 75° C.

In another preferred embodiment, the process for determining the quantitative and qualitative profile according to the present invention is characterized in that the amplification products can be elongated, wherein the elongation products are separated relative to their length. The signal obtained for the elongation products is measured, and the quantitative and qualitative profile of the labeling intensity relative to the elongation product length is established.

The elongation step, also called a run-off reaction, allows one to determine the length of the amplification product. The length can be determined using conventional techniques, for example, using gels such as polyacrylamide gels for the separation, DNA sequencers, and adapted software. Because some mutations display length heterogeneity, some mutations can be determined by a change in length of elongation products.

In one aspect, the invention includes a primer that is complementary to a nucleic acid sequence of the miRNA of interest, and more particularly the primer includes 12 or more contiguous nucleotides substantially complementary to the sequence of the miRNA of interest. Preferably, a primer featured in the invention includes a nucleotide sequence sufficiently complementary to hybridize to a nucleic acid sequence of about 12 to 25 nucleotides. More preferably, the primer differs by no more than 1, 2, or 3 nucleotides from the target nucleotide sequence In another aspect, the length of the primer can vary in length, preferably about 15 to 28 nucleotides in length (e.g., 15, 16, 17, 18, 19, 20, 21, 22, 23, 24, 25, 26, 27 or 28 nucleotides in length).

Treatment

The present invention provides therapeutic molecules for the treatment or prevention of endometriosis. In one embodiment, the therapeutic molecules include but are not limited to inhibitors, activators, and modulators of the markers of the invention. For example, if a gene is downregulated in endometriosis, than it would be desirable to increase the expression of the downregulated gene to normal levels using an activator as a form of therapy. Activators are compounds that increase, open, activate, facilitate, enhance activation, sensitize, agonize, or up regulate activity of endometriosis biomarkers. Alternatively, if a gene is upregulated in endometriosis, than it would be desirable to decrease the expression of the upregulated gene to normal levels using an inhibitor as a form of therapy. Inhibitors are compounds that, e.g., bind to, partially or totally block activity, decrease, prevent, delay activation, inactivate, desensitize, or down regulate the activity or expression of endometriosis biomarkers.

Methods and materials for increasing or decreasing the expression levels of the markers of the present invention are well known and within the skill of a person in the art. A non-limitative list of known methods and materials includes: diet, vitamins, dietary supplements, gene therapy methods, antisense oligonucleotides, drugs and hormonal medications.

Once a patient is diagnosed with having or is at risk of having endometriosis, the patient can be treated using methods known in the art. Well known treatments for endometriosis include, but are not limited to, pain killers, hormonal treatments, chemotherapy, and surgical treatments. Pain killers used for the treatment of endometriosis include both simple analgesics, such as paracetamol, COX-2 inhibitors, aspirin, and other non-steroidal anti-inflammatory drugs well known in the art, and narcotic analgesics, such as morphine, codine, oxycodone, and others well known in the art. Hormonal treatments include, but are not limited to, oral contraceptives, progestins, such as Dydrogesterone, Medroxyprogesterone acetate, Depot medroxyprogesterone acetate, Norethisterone, Levonorgestrel, and others well known in the art, progesterone and progesterone-like substances, GnRH agonists, such as leuprorelin, buserelin, goserelin, histrelin, deslorelin, nafarelin, and triptorelin, androgens and synthetic androgens like Danazol, and aromatase inhibitors. Surgical treatments include, but are not limited to, laparoscopic surgery, hysterectomy, and oophorectomy. Other treatments particularly well suited for use in the present invention are well known in the art.

Determining Effectiveness of Therapy or Prognosis

In one aspect, the level of one or more circulating miRNAs in a biological sample of a patient is used to monitor the effectiveness of treatment or the prognosis of disease. In some embodiments, the level of one or more circulating miRNAs in a test sample obtained from a treated patient can be compared to the level from a reference sample obtained from that patient prior to initiation of a treatment. Clinical monitoring of treatment typically entails that each patient serve as his or her own baseline control. In some embodiments, test samples are obtained at multiple time points following administration of the treatment. In these embodiments, measurement of level of one or more circulating miRNAs in the test samples provides an indication of the extent and duration of in vivo effect of the treatment.

A prognosis may be expressed as the amount of time a patient can be expected to survive. Alternatively, a prognosis may refer to the likelihood that the disease goes into remission or to the amount of time the disease can be expected to remain in remission. Prognosis can be expressed in various ways; for example, prognosis can be expressed as a percent chance that a patient will survive after one year, five years, ten years or the like. Alternatively, prognosis may be expressed as the number of years, on average that a patient can expect to survive as a result of a condition or disease. The prognosis of a patient may be considered as an expression of relativism, with many factors affecting the ultimate outcome. For example, for patients with certain conditions, prognosis can be appropriately expressed as the likelihood that a condition may be treatable or curable, or the likelihood that a disease will go into remission, whereas for patients with more severe conditions prognosis may be more appropriately expressed as likelihood of survival for a specified period of time. Additionally, a change in a clinical factor from a baseline level may impact a patient's prognosis, and the degree of change in level of the clinical factor may be related to the severity of adverse events. Statistical significance is often determined by comparing two or more populations, and determining a confidence interval and/or a p value.

Multiple determinations of circulating miRNA levels can be made, and a temporal change in activity can be used to determine a prognosis. For example, comparative measurements are made of the circulating miRNA of an acellular body fluid in a patient at multiple time points, and a comparison of a circulating miRNA value at two or more time points may be indicative of a particular prognosis.

In certain embodiments, the levels of activity of one or more circulating miRNAs are used as indicators of an unfavorable prognosis. According to the method, the determination of prognosis can be performed by comparing the measured circulating miRNA level to levels determined in comparable samples from healthy individuals or to levels known to corresponding with favorable or unfavorable outcomes. The circulating miRNA levels obtained may depend on an number of factors, including, but not limited to, the laboratory performing the assays, the assay methods used, the type of body fluid sample used and the type of disease a patient is afflicted with. According to the method, values can be collected from a series of patients with a particular disorder to determine appropriate reference ranges of circulating miRNA for that disorder. One of ordinary skill in the art is capable of performing a retrospective study that compares the determined levels to the observed outcome of the patients and establishing ranges of levels that can be used to designate the prognosis of the patients with a particular disorder. For example, levels in the lowest range would be indicative of a more favorable prognosis, while circulating miRNA levels in the highest ranges would be indicative of an unfavorable prognosis. Thus, in this aspect the term "elevated levels" refers to levels of that are above the range of the reference value. In some embodiments patients with "high" or "elevated" levels have levels that are higher than the median activity in a population of patients with that disease. In certain embodiments, "high" or "elevated" levels for a patient with a particular disease refers to levels that are above the median values for patients with that disorder and are in the upper 40% of patients with the disorder, or to levels that are in the upper 20% of patients with the disorder, or to levels that are in the upper 10% of patients with the disorder, or to levels that are in the upper 5% of patients with the disorder.

Because the level of circulating miRNA in a test sample from a patient relates to the prognosis of a patient in a continuous fashion, the determination of prognosis can be performed using statistical analyses to relate the determined circulating miRNA levels to the prognosis of the patient. A skilled artisan is capable of designing appropriate statistical methods. For example, the methods may employ the chi-squared test, the Kaplan-Meier method, the log-rank test, multivariate logistic regression analysis, Cox's proportional-hazard model and the like in determining the prognosis. Computers and computer software programs may be used in organizing data and performing statistical analyses. The approach by Giles et. al., British Journal of Hemotology, 121:578-585, is exemplary. As in Giles et al., associations between categorical variables (e.g., miRNA levels and clinical characteristics) can be assessed via cross-tabulation and Fisher's exact test. Unadjusted survival probabilities can be estimated using the method of Kaplan and Meier. The Cox proportional hazards regression model also can be used to assess the ability of patient characteristics (such as miRNA levels) to predict survival, with 'goodness of fit' assessed by the Grambsch-Therneau test, Schoenfeld residual plots, martingale residual plots and likelihood ratio statistics (see Grambsch et al, 1995). In some embodiments, this approach can be adapted as a simple computer program that can be used with personal computers or personal digital assistants (PDA). The prediction of patients' survival time in based on their circulating miRNA levels can be performed via the use of a visual basic for applications (VBA) computer program developed within Microsoft Excel. The core construction and analysis may be based on the Cox proportional hazard models. The VBA application can be developed by obtaining a base hazard rate and parameter estimates. These statistical analyses can be performed using a statistical program such as the SAS proportional hazards regression, PHREG, procedure. Estimates can then be used to obtain probabilities of surviving from one to 24 months given the patient's covariates. The program can make use of estimated probabilities to create a graphical representation of a given patient's predicted survival curve. In certain embodiments, the program also provides 6-month, 1-year and 18-month survival probabilities. A graphical interface can be used to input patient characteristics in a user-friendly manner.

In some embodiments of the invention, multiple prognostic factors, including circulating miRNA level, are considered when determining the prognosis of a patient. For example, the prognosis of a cancer patient may be determined based on circulating miRNA and one or more prognostic factors selected from the group consisting of cytogenetics, performance status, age, gender and previous diagnosis. In certain embodiments, other prognostic factors may be combined with the circulating miRNA level or other biomarkers in the algorithm to determine prognosis with greater accuracy.

Kits

The present invention also pertains to kits useful in the methods of the invention. Such kits comprise components useful in any of the methods described herein, including for example, hybridization probes or primers (e.g., labeled probes or primers), reagents for detection of labeled molecules, oligonucleotide arrays, restriction enzymes, antibodies, allele-specific oligonucleotides, means for amplification of a subject's nucleic acids, means for reverse transcribing a subject's RNA, means for analyzing a subject's nucleic acid sequence, and instructional materials. For example, in one embodiment, the kit comprises components useful for the detection and quantification of at least one miRNA associated with endometriosis. In a preferred embodiment of the invention, the kit comprises components for detecting one or more of the miRNAs associated with endometriosis as elsewhere described herein.

The present invention also provides kits for diagnosing endometriosis or reduced fertility caused by endometriosis, comprising a probe for one or more nucleic acid biomarkers known to be differentially expressed in endometriosis. In one particular embodiment, the kit comprises reagents for quantitative amplification of the selected biomarkers. Alternatively, the kit may comprise a microarray. In some embodiments the kit comprises 2 or more probes. In other embodiments, the kits may contain 3, 4, 5, 6, 7, 8, 9, 10, 15, 20, 25, or more probes.

The present invention also pertains to kits useful in the methods of the invention. Such kits comprise various combinations of components useful in any of the methods described elsewhere herein, including for example, materials for quantitatively analyzing a biomarker of the invention (e.g., polypeptide and/or nucleic acid), materials for assessing the activity of a biomarker of the invention (e.g., polypeptide and/or nucleic acid), and instructional material. For example, in one embodiment, the kit comprises components useful for the quantification of a desired nucleic acid in a biological sample.

In a further embodiment, the kit comprises the components of an assay for monitoring the effectiveness of a treatment administered to a subject in need thereof, containing instructional material and the components for determining whether the level of a biomarker of the invention in a biological sample obtained from the subject is modulated during or after administration of the treatment. In various embodiments, to determine whether the level of a biomarker of the invention is modulated in a biological sample obtained from the subject, the level of the biomarker is compared with the level of at least one comparator control contained in the kit, such as a positive control, a negative control, a historical control, a historical norm, or the level of another reference molecule in the biological sample. In certain embodiments, the ratio of the biomarker and a reference molecule is determined to aid in the monitoring of the treatment.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Circulating microRNAs as Potential Biomarkers for Endometriosis

The results presented herein demonstrate that the levels of circulating let-7b and miR-135a were statistically significantly decreased in women with endometriosis compared with controls, and let-7d and 7f showed a trend toward down-regulation. Let-7b expression strongly correlated with serum CA-125 levels and showed the highest area under the curve of 0.691. When the patients were analyzed according to phase of the menstrual cycle, the expression of let-7b, 7c, 7d, and 7e was statistically significantly lower in the women with endometriosis during the proliferative phase. Using a logistic regression model, experiments were designed to evaluate the diagnostic power of differently expressed miRNAs; the combination of let-7b, let-7d, and let-7f during the proliferative phase yielded the highest area under the curve value of 0.929 in discriminating endometriosis from controls.

It was observed that several circulating miRNAs are differentially expressed in the sera of women with endometriosis compared with controls. The combination of serum let-7b, 7d, and 7f levels during the proliferative phase serves as a diagnostic marker for endometriosis.

The materials and methods employed in this example are now described.

Materials and Methods

Study Population

Forty eight women aged 18 to 48 years participated in this study after giving written informed consent. The study was approved by the institutional review board of Gangnam Severance Hospital and the Yale University School of Medicine. Volunteers were recruited among patients who underwent laparoscopy for various indications, including pelvic masses, pelvic pain, endometriosis, infertility, and diagnostic evaluation of benign gynecologic disease. Women were recruited when the following criteria were met: aged 20 to 50 years, no hormone therapy for at least 3 months, non-smoker, without a history or signs of other inflammatory disease, who were undergoing surgical treatment/exploration. The exclusion criteria included postmenopausal status; previous hormone or gonadotropin-releasing hormone (GnRH) agonist use; adenomyosis; endometrial cancer, hyperplasia, or endometrial polyps; infectious diseases; chronic or acute inflammatory diseases; malignancy; autoimmune disease; and cardiovascular disease. Pretreatment serum CA-125 levels in all patients were measured using CA-125 II electro-chemiluminescence immunoassay (ECLIA) with the Roche/Hitachi Modular Analytics E170 system (Roche Diagnostics).

Before surgery, clinical data from each individual were collected, including alcohol usage and comorbidities. Concerning classifying alcohol users and nonusers, the group was divided into nondrinking or drinking individuals, but no attempts were made to identify the frequency of alcohol use. All patients had regular menstrual cycles, and the menstrual cycle stage was recorded for each patient as either proliferative phase (from the beginning of menses until 14 days before the next menses) or secretory phase (1-13 days before the next menses).

At the time of surgery, all possible endometriotic lesions were excised and sent for pathology examination for confirmation of the diagnosis. Patients were assigned to the endometriosis group only after pathologic confirmation of the excised tissue. The extent of endometriosis was determined using the American Society of Reproductive Medicine (ASRM) revised classification (American Society for Reproductive Medicine, 1997, Fertil Steril, 67: 817-821). Twenty-four patients had histologically confirmed peritoneal and/or ovarian endometriosis, with moderate-to-severe disease (stages III and IV). Twenty-four patients participated as controls, which included 10 cases of dermoid cysts (n=10), serous cystadenoma (n=5), mucinous cystadenoma (n=3), simple ovarian cysts (n=3), and paratubal cysts (n=1).

Sample Collection and RNA Extraction

All patients abstained from food for at least 8 hours before surgery. Before anesthesia, blood samples were collected into 10-mL sterile tubes containing no additives. The samples were immediately centrifuged at 1,000×g for 10 minutes, and sediment-free serum samples were obtained. The serum aliquots were frozen at −80° C. until further analysis and thereafter were thawed only once. The total RNA was extracted from 400 μL of serum using the miR-Vana RNA Isolation Kit (Applied Biosystems) according to the manufacturer's specifications, and was eluted with 50 μL of nuclease-free water. The yield of RNA was determined using a NanoDrop ND-2000spectrophotometer (Nanodrop Technologies).

Quantitative Real-Time Polymerase Chain Reaction for miRNAs

We employed the Poly (A) reverse-transcription polymerase chain reaction method using an Invitrogen NCode miRNA First-Strand cDNA Synthesis MIRC-50 kit (Life Technologies) following the manufacturer's instructions. Total RNA (25 ng) from each sample was reverse transcribed, and the miRNAs were quantified using the iQ SYBR Green supermix kit (Bio-Rad Laboratories) with the specific forward primers for let-7a-f, miR-135a, and miR-135b, and the universal reverse primer complementary to the anchor primer. The reaction mixture included 2.5 μL of cDNA, 12.5 μL of iQSYBR Green Supermix, 1.0 μL of forward primer, 1 μL of universal quantitative polymerase chain reaction primer, and 8 μL of RNase-free water for a final reaction volume of 25 μL. The thermal cycling conditions were initiated by uracil-N-glycosylase activation at 50° C. for 2 minutes and initial denaturation at 95° C. for 10 minutes, followed by 40 cycles at 95° C. for 15 seconds and annealing at 60° C. for 20 seconds. Threshold cycle and melting curves were acquired by using the quantitation and melting curve program of the Bio-Rad iCycleriQsystem (Bio-Rad Laboratories). Anchor reverse-transcription primer was used as the template for negative control, and U6 small nuclear RNA was used as a control to determine relative miRNA expression (Kuwabara et al., 2011, Circ Cardiovasc Genet, 4: 446-454; Zhang et al., 2010, Clin Chem, 56: 1830-1838). The relative mRNA level was determined using the formula $2^{-\Delta CT}$. Primers for let-7a-f, miR-135a, miR-135b, and the U6 genes were obtained from the W. M. Keck Oligonucleotide Synthesis Facility (Yale University): let-7a forward, TGAGGTAGTAGG-TTGTATAGTT (SEQ ID NO: 9); let-7b forward, TGAGGTAGTAGGTTGTGTGGTT (SEQ ID NO: 10); let-7c forward, TGAGGTAGTAGGTTGTATGGTT (SEQ ID NO: 11); let-7d forward, AGAGGTAGTAGGTTGCAT-AGTT (SEQ ID NO: 12); let-7e forward, TGAGGTAG-GAGGTTGTATAGTT (SEQ ID NO: 13); let-7f forward, TGAGGTAGTAGATTGTATAGTT (SEQ ID NO: 14); miR-135a forward, TATGGCTTTTTATTCCTATGTGA (SEQ ID NO: 15); mi-135b reverse, TATGGCTTTTCATTCC-TATGTGA (SEQ ID NO: 16); and U6 forward, CTCGCTTCGGCAGCACA (SEQ ID NO: 17), reverse, AACGCTTCACGAATTTGCGT (SEQ ID NO: 18).

Statistical Analysis

Data were expressed as mean±standard deviation (SD) or median (interquartile range) where appropriate. Student's t-test was used to determine the statistical significance of differences in clinical characteristics between the endometriosis and control groups. The expression levels of serum miRNAs between the groups were compared using the Mann-Whitney U test. To determine the significance of differences in correlations, Pearson's correlation coefficient or Spearman rank correlation coefficient were calculated, where appropriate.

The diagnostic performance of miRNA expression levels was assessed using receiver operating characteristic (ROC) curves to plot the test sensitivity versus its false-positive rate and determine the usefulness of a diagnostic test over a range of possible clinical results (Hanley et al., 1982, Radiology, 143: 29-36). The diagnostic utility of the test can be expressed as the area under the ROC curve (AUC), which was calculated as a measure of the ability of each potential biomarker to discriminate between endometriosis and control cases. An AUC of 0.5 indicates classifications assigned by chance. Based on ROC analysis, the best statistical cutoff value of miRNA expression level was calculated, which corresponds to the point at which the sum of false positives and false negatives is less than any other point. The sensitivity and specificity for the selected cutoff points were then assessed.

To assess the diagnostic power of multiple combinations of miRNAs expression levels, a logistic regression model was applied. SPSS 16.0 (SPSS Inc, Chicago, Ill.) was used for statistical analysis. $P<0.05$ was considered statistically significant.

The results of the experiments are now described.

Clinical Characteristics

The clinical characteristics of the participants are shown in Table 1. The mean age (±SD) of patients with endometriosis and controls was 33.08±6.63 years and 32.16±9.46 years, respectively. There were no statistically significant differences in parameters such as mean age, gravidity, parity, alcohol usage, or comorbidities between the two groups. Comorbidities included one case with hyperthyroidism and one case of duodenal ulcer in control group, and one case of hyperthyroidism and one case of hypothyroidism in the endometriosis group. By contrast, the visual analogue scale (VAS) score for pelvic pain intensity and serum CA-125 levels was statistically significantly higher in the women with endometriosis than in the controls (5.40±3.37 vs. 2.08±2.39, and 103.25±121.75 vs. 17.48±6.28 IU/mL, respectively; P=0.003) (Mol et al., 1998, Fertil Steril, 70: 1101-1108). In this referral population, all endometriosis patients had moderate-to-severe disease with mean revised ASRM scores of 53.93. All 24 patients had ovarian endometriosis. Among these patients, 22 patients had coexisting peritoneal disease, and 8 individuals were also considered to have lesions of deep infiltrating endometriosis (see Table 1).

TABLE 1

Clinical characteristics of study participants with and without endometriosis (controls).

| Characteristic | Endometriosis (n = 24) | Control (n = 24) | P value |
|---|---|---|---|
| Age (y) | 33.08 ± 6.63 | 32.16 ± 9.46 | .700 |
| Gravidity | 1.41 ± 1.58 | 1.29 ± 1.39 | .773 |
| Parity | 0.71 ± 0.85 | 0.79 ± 0.93 | .749 |
| Alcohol usage | 0 | 3 (12.5%) | .234 |
| Comorbidities | 2 (8.3%) | 2 (8.3%) | 1.000 |
| Pain intensity (VAS) | 5.40 ± 3.37 | 2.08 ± 2.39 | <.001 |
| CA-125 (IU/mL) | 103.25 ± 121.75 | 17.48 ± 6.28 | .003 |
| rASRM stage | | | |
| III (n) | 11 (45.8%) | NA | |
| VI (n) | 13 (54.2%) | NA | |
| rASRM scores | 53.93 ± 6.02 | NA | |
| Distribution of endometriosis | | | |
| Ovarian endometrioma | 24 (100.0%) | NA | |
| Peritoneal lesion | 22 (91.6%) | NA | |
| DIE status | | | |
| With DIE lesions | 8 (33.3%) | NA | |
| Without DIE lesions | 16 (66.7%) | NA | |

Note:
Data are expressed as mean ± standard deviation or n (%). DIE = deeply infiltrating endometriosis; NA = not applicable; rASRM = revised American Society for Reproductive Medicine guidelines; VAS = visual analogue scale.

Figure 4:
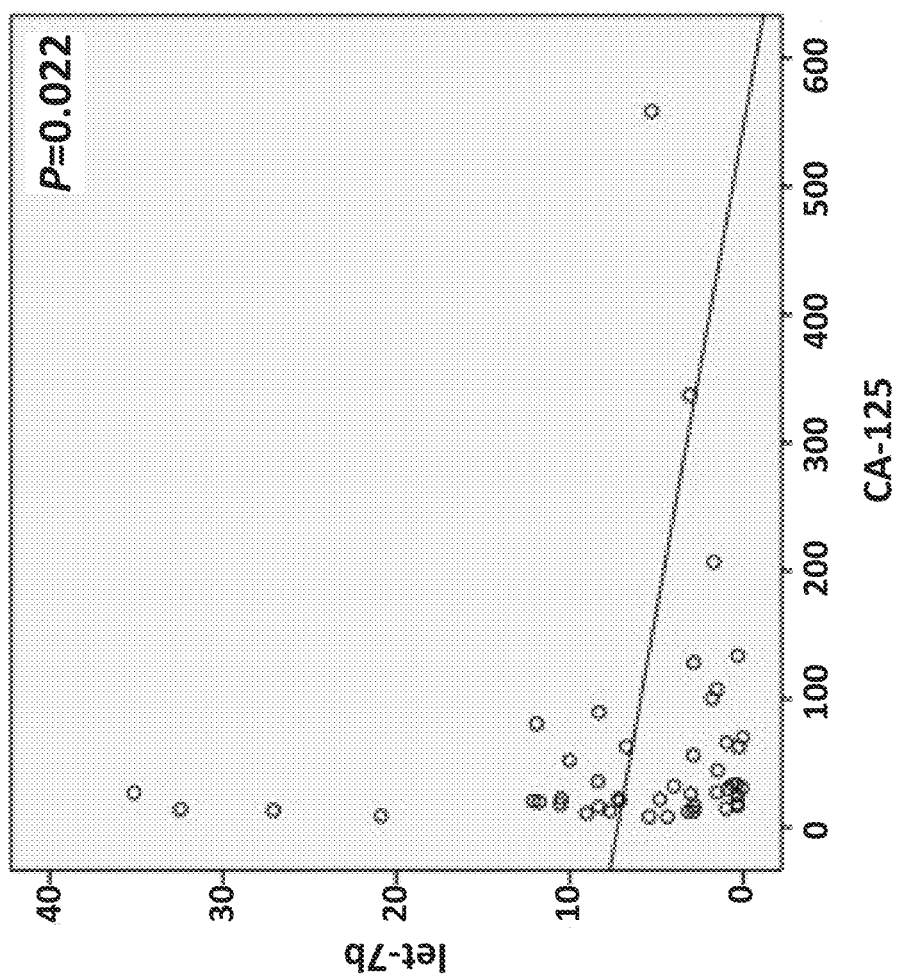
FIG. 4 is an image showing the correlations between let-7b expression levels and serum CA-125 levels. A significant negative correlation was noted ($r=-0.333$).

Expression of Circulating miRNAs in Sera of Patients with and without Endometriosis The relative expressions of let-7a-f, miR-135a, and miR-135b in the serum of patients with and without endometriosis were assessed using quantitative real-time polymerase chain reaction. Among those miRNAs, the expression levels of let-7b and miR-135a were statistically significantly lower in patients with endometriosis than in controls (3.2-fold differences, P=0.021 and 2.0-fold differences, P=0.025, respectively), while the expression of let-7d and lef-7f showed a trend toward down-regulation (FIG. 1). When correlations between miRNA expressions and clinical parameters were evaluated, there was statistically significant negative correlations between let-7b expression levels and serum CA-125 levels (P=0.022, r=−0.333) (FIG. 4), but no other clinical parameters showed statistically significant correlations with miRNA expression levels. Notably, when the correlations between expression levels of let-7 subtypes and miR-135 were evaluated, all let-7 subtypes including let-7a, let-7b, let-7c, let-7d, let-7e, and let-7f displayed strong positive correlations with miR-135a expression levels (r=0.512, r=0.576, r=0.413, r=0.449, r=0.490 and r=0.643, respectively) with statistical significance (P<0.001, P<0.001, P=0.004, P=0.002, P=0.001, and P<0.001, respectively).

Evaluation of Target Gene Prediction for Let-7b and Mir-135a

Using the StarBase database (Li et al., 2014, Nucleic Acids Res, 42: D92-D97), target genes for differently expressed miRNAs between endometriosis and controls were predicted. For let-7b, 321 genes were predicted as target sites, including several genes that are known to be dysregulated in cancerous conditions and other diseases such as CCND1, HOXA9, TGFBR1, and HMGA2. Interestingly, functional annotation analysis indicated that 15 of these genes are involved in p53 signaling pathway (CASP3, CCND1, CCND2, CDKN1A, FAS, RRM2, and THBS1) and cell cycle (CCND1, CCND2, CDC25A, CDKN1A, E2F5, ESPL1, SMC1A, and YWHAZ), suggesting that let-7b may play a role in endometriosis by influencing the function of p53 proteins and cell cycle control. For mir-135a, 62 genes were predicted as targets sites including HOXA10, VLDLR, and CSF1. An association between mir-135a and HOXA10 in endometriosis and ovarian cancer has been documented previously (Petracco et al., 2011, J Clin Endocrinol Metab, 96: E1925-E1933; Tang et al., 2014, Cell Signal, 26: 1420-1426). It has been shown that mir-135a functions as a tumor suppressor in epithelial ovarian cancer by regulation of HOXA10 expression (Tang et al., 2014, Cell Signal, 26: 1420-1426) and acts as a putative tumor suppressor by directly targeting VLDLR in human gallbladder cancer (Zhou et al., 2014, Cancer Sci, 105: 956-965). Also, several targeted genes are known to be involved in positive regulation of apoptotic process (DDX3X, NET1, NF1, TCF7L2, and TXNIP) and Wnt signaling pathways (FZD1, NFAT5, TBL1XR1, TCF7L2).

Expression of Circulating miRNAs According to the Menstrual Cycle

Figure 2:
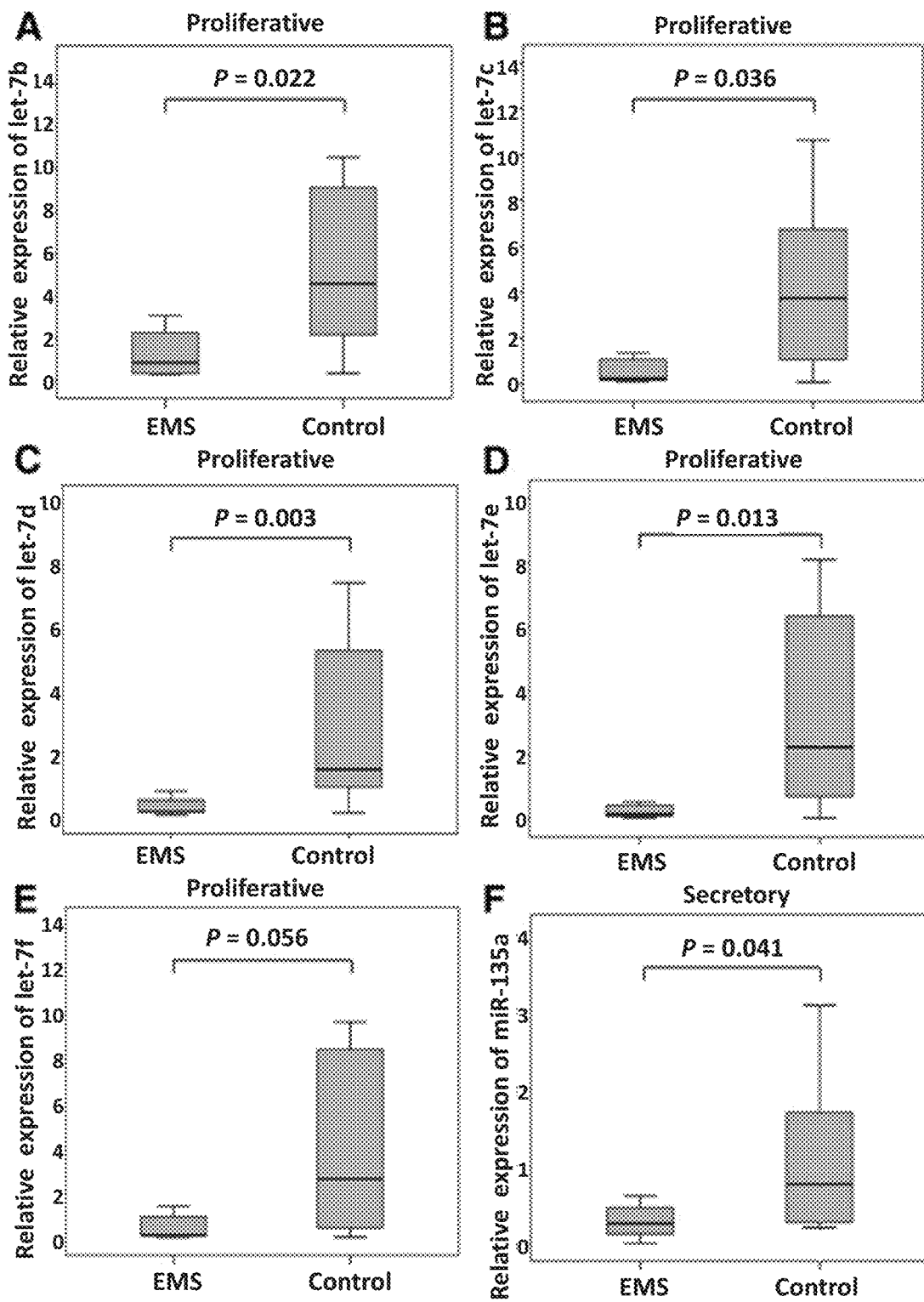
FIG. 2, comprising

When the relative expressions of miRNAs in patients with and without endometriosis were evaluated according to the menstrual cycle, several miRNAs were found to be expressed differently in endometriosis patients. The expression of let-7a, let-7d, let-7e, and let-7f were statistically significantly higher during the secretory phase (P=0.018, P=0.033, P=0.039, and P=0.039, respectively) whereas no cyclic differences in miRNA expression were noted in the control group. When miRNA expression was compared between the endometriosis and control groups according to the menstrual cycle, let-7b, let-7c, let-7d, and let-7e were statistically significantly down-regulated in the endometriosis patients compared with the controls (5.3-fold, 16.9-fold, 9.9-fold, and 14.0-fold, respectively) during the proliferative phase (P=0.022, P=0.036, P=0.003, and P=0.013, respectively), and the expression of let-7f showed a trend toward down-regulation (FIG. 2). During the secretory phase, the expression of miR-135a was statistically significantly lower in the women with endometriosis compared with the controls (2.9-fold, P=0.041) (see FIG. 2).

Assessment of the Diagnostic Value of Circulating miRNAs in Endometriosis

To assess the utility of circulating miRNAs in diagnosing endometriosis, we examined the ROC curve of serum miRNA, which was differentially expressed between endometriosis patients and controls. The AUC of let-7b and miR-135a was 0.694 (95% confidence interval [CI], 0.543-0.844) and 0.690 (95% CI, 0.540-0.841), respectively. Because several miRNAs were found to be differentially expressed when comparing endometriosis patients and controls according to the menstrual cycle, we examined the ROC curve of let-7b, let-7c, let-7d, and let-7e during the proliferative phase and that of miR-135a during the secretory phase. The AUC of let-7b, let-7c, let-7d, and let-7e during the proliferative phase was 0.821 (95% CI, 0.599-1.000), 0.798 (95% CI, 0.584-1.000), 0.905 (95% CI, 0.000-1.000), and 0.845 (95% CI, 0.000-1.000), respectively. The AUC of miR-135a during the secretory phase showed 0.741 (95% CI, 0.549-0.933). Because let-7d expression levels yielded the highest AUC among others, the sensitivity and specificity for let-7d expression levels were calculated, and it displayed a sensitivity and specificity of 83.3% and 100.0%, respectively, at the cutoff value of 0.823 in discriminating endometriosis from controls.

Figure 3:
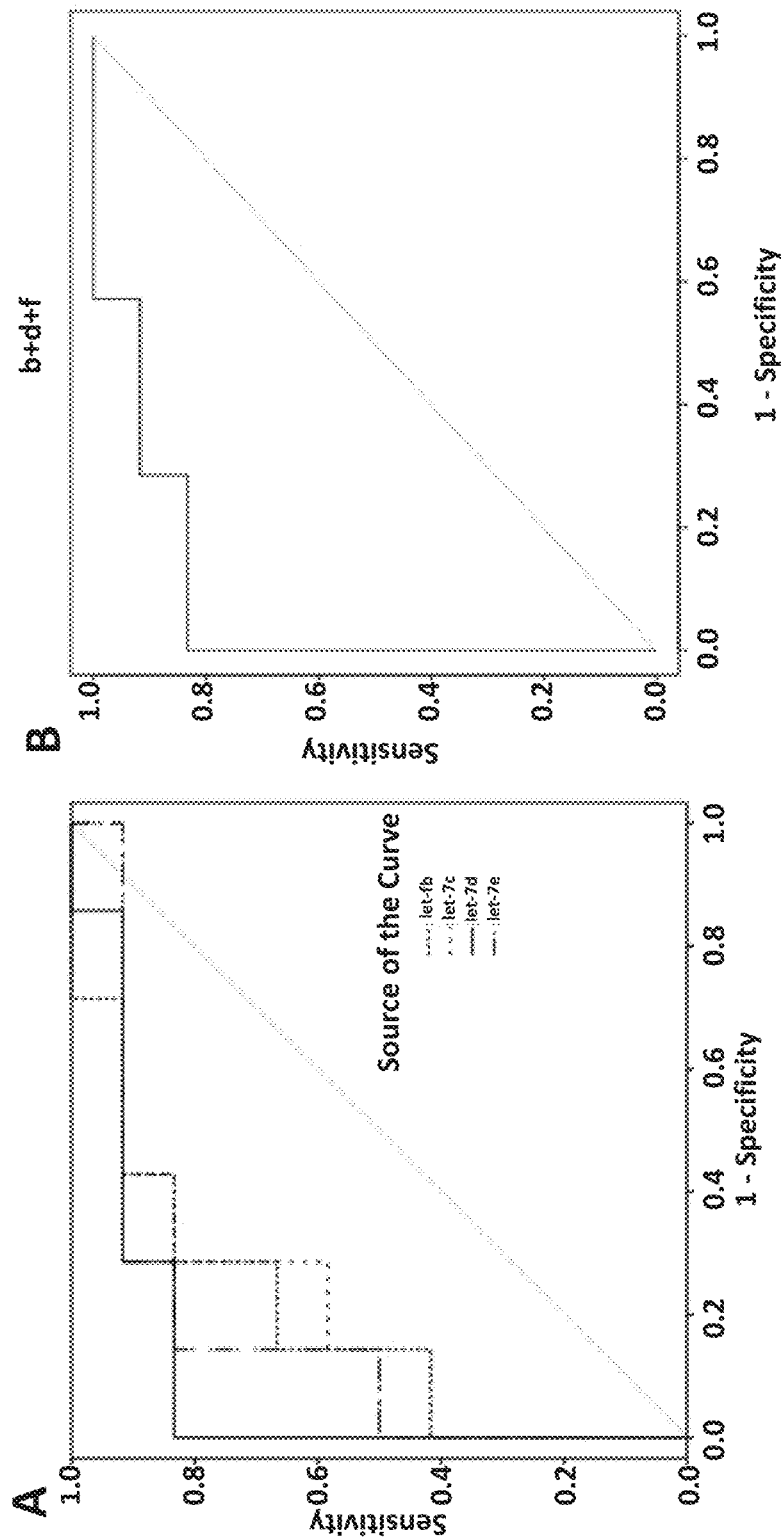
FIG. 3, comprising

To improve the diagnostic power of miRNA expressions during the proliferative phase, the logistic regression model was applied to the data for disease versus control samples. Different combinations of predictors were fed to the model, and the maximum AUC score of 0.929 was achieved when using the predictors let-7b, let-7d, and let-7f (FIG. 3). The fitted logistic regression model is as follows:

$$logit\frac{P(Y=1)}{1-P(Y=1)} = -2.08249 - 0.28299*b + 4.90579*d - 0.09363*f$$

where P(Y=1) is the probability of a proliferative stage sample being a disease sample.

Circulating Let-7 and miR-135 Family Members as Biomarkers for Endometriosis

In the present study, the expression of circulating let-7 and miR-135 family members was evaluated as potential biomarkers for endometriosis. The results showed that the expression of let-7b and miR-135a was statistically significantly down-regulated in patients with endometriosis compared with women without the disease. Experiments were also conducted to evaluate the cyclic differences of these miRNAs and discovered that the expression of several miRNAs was different when comparing endometriosis patients and controls according to stage of the menstrual cycle. Although the study population included a relatively high prevalence of endometriosis, when the diagnostic power of differentially expressed miRNAs was evaluated, let-7d expression during the proliferative phase showed a sensitivity and specificity of 83.3% and 100.0%, respectively, at a cutoff value of 0.823. In addition, the combination of let-7b, let-7d, and let-7f during the proliferative phase yielded even higher diagnostic potentials, using the logistic regression model with an AUC of 0.929.

It is interesting that the results showed that let-7b expression levels were statistically significantly lower in patients with endometriosis than in controls, and statistically significant negative correlations between the expression levels of let-7b and serum CA-125 was observed.

The expression of circulating miR-135a was statistically significantly lower in patients with endometriosis, and the expression level was positively correlated with let-7 family expression. It is interesting that both miR-135a and miR-135b were overexpressed in the endometrium of patients with endometriosis compared with controls, and increased expression of these miRNAs in endometriosis led to the suppression of genes required for implantation (Petracco et al., 2011, J Clin Endocrinol Metab, 96: E1925-E1933). There is no clear explanation for the discrepancy between the tissue and serum levels. Although the correlation of miRNA expression between tissues and circulation has been noted in various conditions, discordance in miRNA expression patterns also has been reported (Jarry et al., 2014, Mol Oncol, 8: 819-829). Moreover miR-135a functions differently in some tumor lineages, acting as an oncomiR in colorectal cancers through inactivation of the adenomatous polyposis *coli*, and as a tumor suppressor in ovarian cancer by regulation of HOXA10 expression (Tang et al., 2014, Cell Signal, 26: 1420-1426; Nagel et al., 2008, Cancer Res, 68: 5795-5802). These miRNAs may be express differently and have distinct functions that depend on the environment and specific tissue types.

It is interesting that the present functional annotation analysis revealed several genes that are predicted target sites for both let-7b and mir-135a, and some of these genes were identified as BACH1 and IGF2BP1. BACH1 is a transcriptional repressor of the hemeoxygenase 1 (HMOX1), which is known as a key cytoprotective enzyme involved in catalyzing heme degradation and acting as an antioxidant (Zhu et al., 2008, Hepatology, 48: 1430-1439); it has been shown that let-7b miRNA directly acts on the 3'-UTR of BACH1 and negatively regulates expression of this protein, thereby up-regulating HMOX1 gene expression and increasing resistance against oxidant injury (Hou et al., 2012, Biochim Biophys Acta, 1819: 1113-1122). IGF2BP1 belongs to a conserved family of RNA-binding, oncofetal proteins involved in cell polarization, migration, morphology, metabolism, proliferation, and differentiation in tumor-derived cells (Bell et al., 2013, Cell Mol Life Sci, 70: 2657-2675); its association with other classic oncogenes, in particular MYC and KRAS has been documented (Mongroo et al., 2011, Cancer Res, 71: 2172-2182). These findings suggest that these miRNAs may be involved in the pathogenesis of endometriosis via regulation of their target genes, and that their protein products may serve as new potential targets for biomarker discovery.

In the present study, statistically significantly lower expression of several miRNAs in sera from women with endometriosis compared with controls was observed. However, the exact origin of these changes in the circulation is not clear. Although evidence suggests that miRNAs may be released from tissues and shed into the circulation (Resnick et al., 2009, Gynecol Oncol, 112: 55-59; Wang et al., 2010, Gynecol Oncol, 119: 586-593), discrepancies between paired tissue-plasma miRNA expression profiles have been noted, indicating that disease tissue or malignant tumor cells are not the sole source of circulating miRNAs (Suryawanshi et al., 2013, Clin Cancer Res, 19: 1213-1224). The concentration of miRNAs in the circulation is not simply a reflection of the tissue level; rather, it more likely depends on the complex regulatory relationship between miRNAs and the possible regulatory relationship between tissues. Although they are still poorly understood, circulating miRNAs may function to signal between tissues; circulating levels reflect the net production from multiple sources in a complex regulatory network.

The present analysis showed a higher AUC when a combination of two or more circulating miRNAs was used, and the diagnostic power of the combined marker was higher than those of commonly used diagnostic indexes of endometriosis, such as CA-125, interleukin-8, interleukin-6, tumor necrosis factor-α, high sensitivity C-reactive protein, and CA-19-9 (Mol et al., 1998, Fertil Steril, 70: 1101-1108; May et al., 2010, Hum Reprod Update, 16: 651-674).

This is the first study to evaluate the cyclic differences of circulating miRNAs in endometriosis. The best AUC was achieved during the proliferative phase after logistic regression. It is interesting that the cyclic variations were noted in the sera of patients with endometriosis and not in women without the disease. These findings are in agreement with a study showing that circulating miRNA levels do not fluctuate in healthy women throughout the menstrual cycle (Rekker et al., 2013, PLoS One, 8: e81166). Cyclic differences in circulating miRNAs were associated with endometriosis, and they are further evidence of the role of aberrant miRNA regulation as an essential component of endometriosis (Petracco et al., 2011, J Clin Endocrinol Metab, 96: E1925-E1933).

In conclusion, the results demonstrate that let-7b and miR-135a, miRNAs, which we had described previously to be associated with endometriosis (Grechukhina et al., 2012, EMBO Mol Med, 4: 206-217; Petracco et al., 2011, J Clin Endocrinol Metab, 96: E1925-E1933), are detectable in serum samples and are differentially expressed in women with and without endometriosis. The results also demonstrate that the expression of these miRNAs have cyclic differences. The combination of several circulating miRNAs is a potential diagnostic biomarker for endometriosis.

The results presented herein demonstrated that several circulating miRNAs are differentially expressed in sera of patients with endometriosis compared to controls. Although let-7b, let-7c, let-7d and let-7e showed statistical significance compared to normal patients, when optimal AUC were calculated, combination of let7b, let-7d and let-7f showed the highest AUC. Thus, the combination of serum let-7b, let-7d and let-7f levels may potentially serve as a diagnostic marker for endometriosis.

What is claimed is:

1. A noninvasive method of detecting miRNA in a subject, the method comprising:
   (a) providing a biological sample comprising saliva from the subject, wherein the subject has endometriosis or is suspected of having endometriosis, and wherein the biological sample comprises at least one miRNA that is a biomarker for endometriosis, wherein at least one miRNA that is a biomarker for endometriosis comprises let-7b miRNA; and
   (b) performing an in vitro amplification procedure on the at least one miRNA that is a biomarker for endometriosis; and
   (c) detecting a level of the at least one miRNA that is a biomarker for endometriosis in the biological sample comprising saliva from the subject; and
   (d) treating the subject for endometriosis based on the detected level of the at least one miRNA that is a biomarker for endometriosis in the biological sample comprising saliva from the subject, wherein the treating the subject comprises administering a hormonal treatment, an oral contraceptive, a progestin, a GnRH agonist, an androgen, an aromatase inhibitor, a non-steroidal anti-inflammatory drug, or a combination thereof, wherein the detected level of the let-7b miRNA is downregulated, and wherein the downregulation is statistically significant.

2. The method of claim 1, wherein the method further comprises detecting at least one miRNA selected from the group consisting of let-7a, let-7c, let-7d, let-7e, let-7f, mir135a, and mir135b.

3. The method of claim 1, wherein the method further comprises detecting at least one miRNA selected from the group consisting of let-7d and let-7f.

4. The method of claim 1, wherein the subject is human.

5. The method of claim 1, wherein the in vitro amplification procedure comprises at least one technique selected from the group consisting of reverse transcription, PCR, sequencing and a microarray.

6. The method of claim 1 wherein the treating the subject comprises administering an oral contraceptive to the subject.

7. The method of claim 1, wherein the treating the subject comprises administering a progestin to the subject.

8. The method of claim 1, wherein the treating the subject comprises administering to the subject a GnRH agonist, an androgen, an aromatase inhibitor, a non-steroidal anti-inflammatory drug, or combination thereof.

9. The method of claim 1, wherein the detected level of the at least one miRNA that is a biomarker for endometriosis is a statistically significant indication of endometriosis.

10. The method of claim 1, wherein the biological sample is acellular.

11. The method of claim 1, wherein the method is at least 90% sensitive for detecting endometriosis.

12. The method of claim 1, wherein the method is at least 90% specific for detecting endometriosis.

13. The method of claim 1, wherein the method is at least 90% accurate for detecting endometriosis.

14. The method of claim 1, wherein a source of the at least one miRNA is an exosome.

15. The method of claim 1, wherein the at least one miRNA is detected at multiple time points.

16. The method of claim 1, further comprising diagnosing or providing a prognosis for endometriosis in a subject, based on the detected level of the at least one miRNA that is a biomarker for endometriosis.

17. The method of claim 16, wherein the diagnosing comprises diagnosing endometriosis during a proliferative phase of endometriosis in the subject.

18. The method of claim 1, wherein treating the subject comprises administering a hormonal treatment to the subject.

19. The method of claim 1, wherein the method is at least 80% sensitive for detecting endometriosis.

20. The method of claim 1, wherein the method is at least 80% specific for detecting endometriosis.

21. The method of claim 1, wherein the sample is a saliva sample and further comprising extracting RNA comprising the at least one miRNA that is a biomarker for endometriosis from the saliva sample prior to (b).

22. The method of claim 1, wherein the treating the subject for endometriosis based on the detected level of the at least one miRNA that is a biomarker for endometriosis in the saliva sample comprises administering a progestin to the subject.

23. The method of claim 1, wherein the treating the subject for endometriosis based on the detected level of the at least one miRNA that is a biomarker for endometriosis in the saliva sample comprises administering a GnRH agonist to the subject.

24. The method of claim 1, wherein the in vitro amplification procedure comprises a sequencing assay.

25. The method of claim 24, wherein the sequencing assay is a next generation sequencing assay.

26. A noninvasive method of detecting endometriosis in a subject, the method comprising detecting in a biological sample obtained from a body fluid altered expression of at least one miRNA selected from the group consisting of let-7a, let-7b, and let-7d, in a subject suspected of or having endometriosis; and treating the subject for endometriosis based on the detected level of the at least one miRNA in the subject, wherein the treating the subject comprises administering a hormonal treatment, an oral contraceptive, a progestin, a GnRH agonist, an androgen, an aromatase inhibitor, a non-steroidal anti-inflammatory drug, or a combination thereof, wherein the detected level of let-7a, let-7b, or let-7d is downregulated, and wherein the downregulation is statistically significant.

27. The method of claim 26, wherein the at least one gene comprises let-7b.

28. The method of claim 26, wherein the biological sample is at least one biological sample selected from the group consisting of blood, serum, plasma, saliva, and urine.

29. The method of claim 26, wherein treating the subject comprises administering a hormonal treatment to the subject.

30. The method of claim 26, wherein the at least one miRNA comprises let-7b.

31. The method of claim 26, wherein the biological sample is selected from the group consisting of blood, serum, and plasma.

32. The method of claim 26, wherein the biological sample is serum.

33. The method of claim 26, wherein the biological sample is plasma.

34. The method of claim 26, wherein the method is at least 80% sensitive for detecting endometriosis.

35. The method of claim 26, wherein the method is at least 80% specific for detecting endometriosis.

36. The method of claim 32, wherein the at least one miRNA comprises let-7a or let-7b.

37. The method of claim 33, wherein the at least one miRNA comprises let-7a or let-7b.

38. The method of claim 36, further comprising extracting RNA comprising the at least one miRNA from the serum sample.

39. The method of claim 37, further comprising extracting RNA comprising the at least one miRNA from the plasma sample.

40. The method of claim 32, wherein the at least one miRNA comprises let-7b.

41. The method of claim 33, wherein the at least one miRNA comprises let-7b.

42. The method of claim 40, wherein the detected level of the let-7b is downregulated.

43. The method of claim 41, wherein the detected level of the let-7b is downregulated.

44. The method of claim 38, wherein the treating the subject for endometriosis based on the detected level of the at least one miRNA that is a biomarker for endometriosis in the saliva sample comprises administering a progestin to the subject.

45. The method of claim 39, wherein the treating the subject for endometriosis based on the detected level of the at least one miRNA that is a biomarker for endometriosis in the saliva sample comprises administering a progestin to the subject.

46. The method of claim 38, wherein the treating the subject for endometriosis based on the detected level of the at least one miRNA that is a biomarker for endometriosis in the saliva sample comprises administering a GnRH agonist to the subject.

47. The method of claim 39, wherein the treating the subject for endometriosis based on the detected level of the at least one miRNA that is a biomarker for endometriosis in the saliva sample comprises administering a GnRH agonist to the subject.

48. The method of claim 38, wherein the detecting comprises a sequencing assay.

49. The method of claim 48, wherein the sequencing assay is a next generation sequencing assay.

50. The method of claim 39, wherein the detecting comprises a sequencing assay.

51. The method of claim 50, wherein the sequencing assay is a next generation sequencing assay.

* * * * *